(12) United States Patent
Maliski et al.

(10) Patent No.: US 11,185,500 B2
(45) Date of Patent: Nov. 30, 2021

(54) MULTI-LAYERED HIGH DOSAGE DISSOLVABLE FILM FOR ORAL ADMINISTRATION

(71) Applicant: OAK THERAPEUTICS INC., Oxnard, CA (US)

(72) Inventors: Edward Maliski, Oxnard, CA (US); Zachary Nicolay, Oxnard, CA (US)

(73) Assignee: OAK THERAPEUTICS INC., Oxnard, CA (US)

( * ) Notice: Subject to any disclaimer, the term of this patent is extended or adjusted under 35 U.S.C. 154(b) by 0 days.

(21) Appl. No.: 16/630,683

(22) PCT Filed: Jun. 18, 2018

(86) PCT No.: PCT/US2018/038034
§ 371 (c)(1),
(2) Date: Jan. 13, 2020

(87) PCT Pub. No.: WO2018/236729
PCT Pub. Date: Dec. 27, 2018

(65) Prior Publication Data
US 2020/0268646 A1    Aug. 27, 2020

Related U.S. Application Data

(60) Provisional application No. 62/521,463, filed on Jun. 18, 2017.

(51) Int. Cl.
*A61K 9/00* (2006.01)
*A61K 47/38* (2006.01)
*A61K 47/32* (2006.01)

(52) U.S. Cl.
CPC .............. *A61K 9/006* (2013.01); *A61K 47/32* (2013.01); *A61K 47/38* (2013.01)

(58) Field of Classification Search
CPC .... A61K 9/0056; A61K 9/006; A61K 9/7007; A61K 47/38; A61K 47/32
See application file for complete search history.

(56) References Cited

U.S. PATENT DOCUMENTS

| | | | | |
|---|---|---|---|---|
| 2002/0132008 | A1* | 9/2002 | Mumper | A61K 9/70 424/487 |
| 2009/0110715 | A1* | 4/2009 | Ishii | A61K 9/286 424/439 |
| 2014/0335153 | A1* | 11/2014 | Allen | A61K 9/7007 424/450 |

FOREIGN PATENT DOCUMENTS

| | | | |
|---|---|---|---|
| WO | 2010146601 A1 | 12/2010 | |
| WO | 2016102067 A1 | 6/2016 | |
| WO | WO-2016102067 A1 * | 6/2016 | ........... A61K 31/196 |

* cited by examiner

*Primary Examiner* — Jianfeng Song
(74) *Attorney, Agent, or Firm* — SoCal IP Law Group LLP; Brian S. Tamsut; Jonathan Pearce

(57) ABSTRACT

Multilayer dissolvable film suitable for oral administration, as well as method of use thereof and method of manufacturing thereof. The dissolvable film contains multiple (e.g., two or more) layers, configured such that the active ingredient(s) can be present in a total amount of at least about 30 wt. % (e.g., at least about 250 mg). The dissolvable film is mucoadhesive and capable of dissolving within about 60 seconds when placed in the oral cavity.

5 Claims, 3 Drawing Sheets

MULTI-LAYERED HIGH DOSAGE DISSOLVABLE FILM FOR ORAL ADMINISTRATION

RELATED U.S. APPLICATION DATA

This application claims priority from U.S. Provisional Patent Application 62/521,463 filed on Jun. 18, 2017, the contents of which are incorporated by reference herein it its entirety.

BACKGROUND

The delivery of medicine to a patient orally is often performed using tablets, capsules or liquid solutions. Because the active ingredients of many medicines taste objectionable to most people, the taste of those compounds are often disguised. Also, pills may be hard for many individuals to swallow, particularly individuals suffering from dysphagia. Difficulty swallowing may be particularly acute for individuals who are young, elderly, or others impaired in some way. While liquids may be reasonably easy to swallow, the flavor of an active ingredient in a medication may make a liquid unpalatable, often to an extreme degree.

The taste of active ingredients in a medicine often presents a great challenge to the oral administration of that medicine. When administered as a pill or capsule, coatings may be used to prevent the patient from tasting the unpleasant flavor of an active ingredient contained within the interior of the pill or capsule. However, once a protective coat has been removed or dissolved from a pill, such as due to repeated unsuccessful attempts to swallow the tablet or capsule or due to the need to cut the tablet or capsule to make it smaller, the resulting taste may render swallowing the medicine even more difficult than before. Meanwhile, some tastes or dosages of active medicines may be impractical to mask adequately for delivery in a liquid form.

As an alternative oral delivery mechanism for medicine, soluble films that incorporate active ingredients within a structural polymer matrix have been developed. Such films typically are formed from a polymer binder that provides a dissolvable matrix that incorporates within the molecules of the matrix the desired active ingredient(s). Flavorings may be added to the matrix itself and/or a surface of the matrix to make the film palatable to a patient. Unfortunately, the addition of active ingredients to the matrix undermines the structural and physical integrity of the matrix due to interfering with the matrix structure. Typically, additions to the matrix in excess of approximately thirty percent of the film (by weight) of active ingredients, flavorings, and/or other materials can result in the breakdown of the film. For this reason, dissolvable films can typically only deliver a relatively low dosage of the active ingredient of a medicine relative to the mass of the strip. Attempts to increase the active/structural polymer ratio typically inhibits structural formation of a film or it increases the amount of time needed to dissolve in the mouth. While higher doses of an active ingredient may be incorporated into a strip by increasing the mass of the matrix containing that active ingredient, there are limits to the area and thickness of a strip that may be administered to a patient. For example, increasing the thickness of the oral film (e.g., beyond what is considered to be an oral thin film) may adversely impact the physical properties (e.g., pharmacokinetic metrics) of the film. Because dissolvable films have previously been usable only to deliver low doses of medication, entire categories of medication (such as many pain relief medications and anti-infective medications) requiring high doses are often excluded from delivery via an oral films.

SUMMARY

The invention provides for a dissolvable film suitable for oral administration. The dissolvable film includes: (a) a top layer, (b) a matrix layer, and (c) a bottom layer. The matrix layer includes at least one active ingredient, present in a total amount of at least about 30 wt. % of the dissolvable film. The top layer and the bottom layer contain between them the matrix layer. Each of the top layer, the matrix layer, and the bottom layer is dissolvable. Additionally, at least one of the top layer and the bottom layer includes one or more structural polymers, such that the dissolvable film is mucoadhesive.

The invention also provides for another dissolvable film suitable for oral administration. The dissolvable film includes: (a) a top layer that includes lipid/emulsifier/plasticizer, binding agent, and optionally flavor and/or sweetener, (b) a matrix layer that includes lipid/emulsifier/plasticizer, binding agent, at least one active ingredient, and optionally flavor and/or sweetener, and (c) a bottom layer that includes binding agent. The top layer and the bottom layer contain between them the matrix layer. Additionally, each of the top layer, the matrix layer, and the bottom layer is dissolvable, and the dissolvable film is mucoadhesive.

The invention also provides for another dissolvable film suitable for oral administration. The dissolvable film includes: a top layer that includes glycerin and at least one of carboxymethylcellulose, Kollidon 90F, Pullulan, hydroxypropyl cellulose, and optionally flavor and/or sweetener, (b) a matrix layer that includes glycerin, active ingredient, and at least one of Kollicoat Protect, hydroxypropyl cellulose, hypromellose, microcrystalline cellulose, Kollidon 90F, and optionally flavor and/or sweetener, and (c) a bottom layer that includes binding agent. The top layer and the bottom layer contain between them the matrix layer. Additionally, each of the top layer, the matrix layer, and the bottom layer is dissolvable, and the dissolvable film is mucoadhesive.

The invention also provides for another dissolvable film suitable for oral administration. The dissolvable film includes: (a) a top layer that includes lipid/emulsifier/plasticizer, binding agent, and optionally flavor and/or sweetener, and (b) a matrix layer that includes lipid/emulsifier/plasticizer, binding agent, at least one active ingredient, and optionally flavor and/or sweetener. The bottom layer contacts the matrix layer, and each of the matrix layer and the bottom layer is dissolvable, and the dissolvable film is mucoadhesive.

The invention also provides for a method that includes administering the dissolvable film described herein to a patient in need thereof. The administration is carried out, in an amount and for a period of time, effective to treat the patient's condition or symptom.

The invention provides for a dissolvable film that possesses one or more advantages. The one or more advantages can be attributed, at least in part, to the structure of the dissolvable film. The structure of the dissolvable film specifically can includes the dissolvable film being multi-layered. In specific embodiments, the multi-layered construction refers to the dissolvable film containing a top layer, a matrix layer, and a bottom layer wherein the top layer and the bottom layer contain between them the matrix layer. In alternative specific embodiments, the multi-layered construction refers to the dissolvable film containing a bottom layer and a matrix layer, wherein the bottom layer contacts the matrix layer.

In additional specific embodiments, each of the top layer, the matrix layer, and the bottom layer is dissolvable. In additional specific embodiments, at least one of the top layer and the bottom layer includes one or more structural polymers, such that the dissolvable film is mucoadhesive. In additional specific embodiments, the active ingredient(s) are encapsulated. In additional specific embodiments, the matrix layer is encapsulated by the top layer and the bottom layer.

With such a construction of the dissolvable film, neither the top layer nor the bottom layer needs to include an appreciable amount of active ingredient. For example, in specific embodiments, neither the top layer nor the bottom layer includes any active ingredient(s). In alternative embodiments, any active ingredient(s) located therein can is less than about 1 wt. % of the dissolvable film.

Such a construction of the dissolvable film allows for the matrix layer to contain a relatively high drug load. For example, in specific embodiments, the matrix layer can include active ingredient(s) present in at least about 25 wt. % of the dissolvable film. In additional embodiments, the matrix layer can include at least about 250 mg active ingredient(s) (and equivalently, the dissolvable film can include at least about 250 mg active ingredient(s)).

Such a construction of the dissolvable film also allows for the structural and physical integrity of the dissolvable film (e.g., each of the top layer, the matrix layer, and the bottom layer) to be effectively maintained. Such a construction of the dissolvable film also allows for the masking of the taste of any active ingredient(s) having an unpleasant taste. Additionally, with such a construction, the requisite mucoadhesiveness of one or both of the top and bottom layer can be maintained.

With such a construction of the dissolvable film, the dissolvable film can maintain the ability to orally disintegrate, thereby rapidly releasing the active ingredient(s) (e.g., within about 45 seconds).

With such a construction of the dissolvable film, the dissolvable film can maintain the requisite mucoadhesion needed during the disintegration, thereby decreasing safety and effectiveness concerns with the patient otherwise swallowing or spitting out the dissolvable film.

With such a construction of the dissolvable film, the dissolvable film can be manufactured while maintaining the physical dimensions, such that it is an oral thin film. As an oral thin film, the dissolvable film will advantageously dissolve quickly when placed in the mouth (e.g., within about 45 seconds) and will possess the requisite pharmacokinetic metrics (e.g., peak plasma concentration after administration (Cmax), time to reach Cmax (tmax), area under the curve (AUC), bioavailability (BA), dose, etc.).

With such a construction of the dissolvable film, the active ingredient(s) can be protected from reacting with (or being exposed to) the environment or degrading due to physical handling.

Such a construction of the dissolvable film also allows for the dissolvable film to be suitable for buccal and/or sublingual administration.

DETAILED DESCRIPTION

Figure 1:
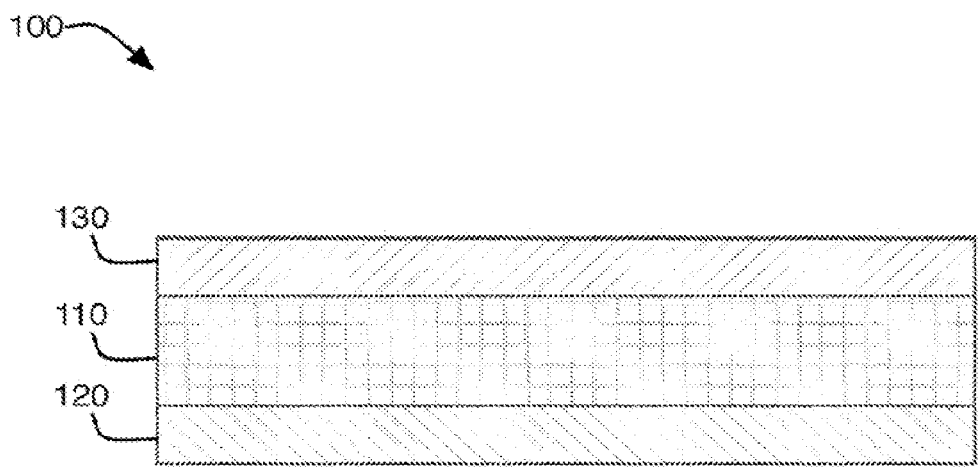
FIG. 1 illustrates a cross-section view of a dissolvable film as described herein.

Reference will now be made in detail to certain claims of the invention, examples of which are illustrated in the accompanying drawings. While the invention will be described in conjunction with the enumerated claims, it will be understood that they are not intended to limit those claims. On the contrary, the invention is intended to cover all alternatives, modifications, and equivalents, which can be included within the scope of the invention as defined by the claims.

References in the specification to "one embodiment," "an embodiment," "an example embodiment," and the like, indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

With the dissolvable films described herein, reference can be made to substances being present therein. These substances are employed in the methods of manufacturing the dissolvable films. However, during the manufacturing process, some of these substances may no longer be present. For example, reference can be made to the dissolvable firm (or more particularly, the base or bottom layer of the dissolvable firm) containing a specified amount of solvent (e.g., water and/or ethanol). During a curing step (which can be carried out at an elevated temperature), some, or all, of the solvent can expectedly evaporate. Unless otherwise specified, reference to the dissolvable film (or any portion thereof) containing specified substance(s), in specified amount(s), will be a reference to the dissolvable film (or portion thereof) being manufactured from the specified substance(s), in the specified amount(s).

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

For example, the step of contacting A with B and/or C includes: (1) contacting A with B, (2) contacting A with C, (3) contacting A with the combination of B+C, (4) contacting A with B, and subsequently contacting that combination (A+B) with C. Additionally, it includes (5) contacting A with C, and subsequently contacting that combination (A+C) with B.

In the methods of manufacturing described herein, unless explicit claim language recites otherwise, the "contacting of A with B" and the "contacting of B with A" will be construed as being the same.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

As used herein, "treat" or "treating" includes preventing, ameliorating, or inhibiting a condition or disorder and/or a symptom of a condition or disorder, of a human patient. The "treatment" (and variations such as "treat" or "treating") refers to clinical intervention in an attempt to alter the natural course of the individual, and can be performed either for prophylaxis or during the course of clinical pathology. Desirable effects of treatment include one or more of preventing the occurrence or recurrence of the condition or disorder, alleviation of symptoms, diminishment of any direct or indirect pathological consequences of the condition or disorder, stabilized (i.e., not worsening) state of condition or disorder, and decreasing the rate of condition or disorder progression. In certain embodiments, the composition described herein is used to: (i) prevent the occurrence or recurrence of the condition or disorder and/or (ii) alleviation of symptoms of the condition or disorder. Those individuals in need of treatment include those already with the condition or disorder or those in which reoccurrence of the condition or disorder is to be prevented.

An "effective amount" of composition described herein refers to an amount effective, at dosages and for periods of time necessary, to achieve the desired therapeutic or prophylactic result. In some embodiments, the effective amount refers to an amount of composition described herein that (i) treats the particular condition or disorder, (ii) attenuates, ameliorates or eliminates one or more symptoms of the particular condition or disorder, or (iii) prevents or delays the onset of one or more symptoms of the particular condition or disorder described herein.

As used herein, "sublingual," "sublingually," "sublingual delivery" or "sublingual administration" refers to the pharmacological route of administration by which substances diffuse into the blood through tissues under the tongue.

As used herein, "buccal," "buccally," "buccal delivery" or "buccal administration" refers to a topical route of administration by which substances held or applied in the buccal area (in the cheek) diffuse through the oral mucosa (tissues which line the mouth) and enter directly into the bloodstream.

Buccal and sublingual administrations may provide better bioavailability of some actives and a more rapid onset of action compared to oral administration because the medication does not pass through the digestive system and thereby avoids first pass metabolism.

The term "substantially" as used herein refers to a majority of, or mostly, as in at least about 50%, 60%, 70%, 80%, 90%, 95%, 96%, 97%, 98%, 99%, 99.5%, 99.9%, 99.999%, or at least about 99.999% or more.

"Oral thin film," "OTF," "oral dissolving film," "oral drug strip," "oral thin film," "thin film," "dissolvable film," "orally dissolvable film strip," or "oral strip" refers to a product used to administer active ingredients via absorption in the mouth (buccally or sublingually), the stomach (gastrically), and/or via the small intestines (enterically). The OTF is edible and pharmaceutically acceptable. A film is prepared typically using hydrophilic polymers that rapidly dissolves on the tongue, palatine tissue, or buccal cavity, delivering the active ingredient to the systemic circulation via dissolution when contact with liquid is made. The OTF (or more appropriately "thin film" or "TF") can also be used to adhere to mucosal tissue (e.g., at least one of mouth, nose, eye, vagina, and rectum), thereby locally delivering the active ingredient(s). As such, it is appreciated that those of skill in the art understand that reference to a thin film for use with mucosal tissue, such as nose, eye, vagina, and rectum, as an "oral thin film" or OTF is appropriate and acceptable.

The term "film" or "dissolvable film" includes thin films and sheets, in any shape, including rectangular, square, or other desired shape. The films described herein may be any desired thickness and size such that it may be placed into the oral cavity of the user. For example, the films may have a relatively thin thickness of from about 0.1 to about 10 mils, or they may have a somewhat thicker thickness of from about 10 to about 30 mils. For some films, the thickness may be even larger, i.e., greater than about 30 mils. The composition in its dried film form can effectively maintain a relatively uniform distribution of components through the application of controlled drying of the film. For example, the film can have no more than a 20%, 10%, 5%, or 1% variance of the active ingredient in the matrix layer, per unit area of the film.

As used herein, "active ingredient" refers to a therapeutic agent and includes any substance, other than food, used in the prevention, diagnosis, alleviation, treatment, or cure of a disease or disorder. *Stedman's Medical Dictionary*, 25$^{th}$ Edition (1990). The substance can be taken by mouth; injected into a muscle, the skin, a blood vessel, or a cavity of the body; or topically applied. *Mosby's Medical, Nursing & Allied Health Dictionary,* 5th Edition (1998). The agent can include any substance disclosed in at least one of: The Merck Index, 15th Edition (2013); PeiShow Juo, *Concise Dictionary of Biomedicine and Molecular Biology*, (1996); US. Pharmacopeia Dictionary, 2000 Edition; *Physician's Desk Reference,* 2017 Edition; *Orange Book: Approved Drug Products with Therapeutic Equivalence Evaluations* (June 2018); and *Approved Animal & Veterinary Drug Products* (*Green Book*) (January 2013). The term active ingredient includes, e.g., prescription and over the counter active pharmaceutical ingredients (e.g., small molecules, macrocycles, peptides, etc.), vitamins, nutraceuticals, supplements (e.g., dietary, nutritional, and herbal), cosmetics, and biologicals.

As used herein, the term "vitamin" refers to an organic compound required by an organism as a vital nutrient in limited amounts. An organic chemical compound (or related set of compounds) is called a vitamin when it cannot be synthesized in sufficient quantities by an organism, and must be obtained from the diet. Thus, the term is conditional both on the circumstances and on the particular organism. For example, ascorbic acid (Vitamin C) is a vitamin for humans, but not for most other animals, and biotin and vitamin D are required in the human diet only in certain circumstances. Examples of human vitamins include Vitamin A (e.g., retinol, retinal, and four carotenoids including beta carotene), Vitamin B1 (thiamine), Vitamin B2 (riboflavin), Vitamin B3 (e.g., niacin and niacinamide), Vitamin B5 (pantothenic acid), Vitamin B6 (e.g., pyridoxine, pyridoxamine, and pyridoxal), Vitamin B7 (biotin), Vitamin B9 (e.g., folic acid and folinic acid), Vitamin B12 (e.g., cyanocobalamin, hydroxocobalamin, and methylcobalamin), Vitamin C (ascorbic acid), Vitamin D (cholecalciferol), Vitamin E (e.g., tocopherols and tocotrienols), and Vitamin K (e.g., phylloquinone, phytonadione, and menaquinones).

Cannabinoids

In specific embodiments, the active ingredient can include one or more cannabinoids. As used herein, "cannabinoid" refer to a compound that acts on cannabinoid receptors in cells that alter neurotransmitter release in the brain. Ligands for these receptor proteins include the endocannabinoids (produced naturally in the body by animals), the phytocannabinoids (found in cannabis and some other plants), and synthetic cannabinoids (manufactured artificially). The most notable cannabinoid is the phytocannabinoid tetrahydrocannabinol (THC), the primary psychoactive compound in cannabis. There are at least 113 different cannabinoids isolated from cannabis plant, exhibiting varied effects. In specific embodiments, the cannabinoid is a cannabinoidergic (e.g., cannabinoid receptor agonist, cannabinoid receptor antagonist, endocannabinoid enhancer (eCBE), or endocannabinoid reuptake inhibitor (eCBRI)).

Suitable cannabinoids include phytocannabinoids (e.g., CBG, CBC, CBD, THC, CBN, CBE, iso-THC, CBL, and CBT) and endocannabinoids (e.g., AEA, 2-AG, noladin ether, NADA, OAE, and LPI). The cannabinoid can specifically be a plant cannabinoid (e.g., cannabigerol-type (CBG), cannabichromene-type (CBC), cannabidiol-type (CBD), cannabinodiol-type (CBND), tetrahydrocannabinol-type (THC), cannabinol-type (CBN), cannabitriol-type (CBT), cannabielsoin-type (CBE), isocannabinoids, cannabicyclol-type (CBL), cannabicitran-type (CBT), or cannabichromanone-type (CBCN)). Alternatively, the cannabinoid can be a synthetic cannabinoid (e.g., Nabilone, Rimonabant, JWH-018, JWH-073, CP-55940, Dimethylheptylpyran, HU-210, HU-331, SR144528, WIN 55,212-2, JWH-133, Levonantradol (Nantrodolum), or AM-2201).

Specifically, the cannabinoid can include at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

Specific suitable cannabinoids include, e.g., CBGA, CBGV, THCA, THCVA, CBDA, CBDVA, CBCA, CBCVA, THC, THCV, CBD, CBDV, CBC, CBG, CBNA, Δ8 THC, and CBN.

The term "lipid/emulsifier/plasticizer" refers to a substance that is a lipid and provides properties as an emulsifier and/or plasticizer. Reference to the substance as a lipid, lipid/emulsifier, or lipid/plasticizer is appropriate.

The term "encapsulate" or "encapsulation" includes partial encapsulation and/or complete (total) encapsulation. It refers to enclosing and/or providing an interface. For example, the encapsulation can be complete, such that matrix layer is enclosed by both the top later and bottom layer, in each of the three physical dimensions: the length (x-axis), the width (y-axis), and height or thickness (z-axis).

Alternatively, the encapsulation can be partial, such that matrix layer is enclosed by the top later and bottom layer in two of the three physical dimensions, the length (x-axis) and the width (y-axis). This can occur, e.g., when a dissolvable film described herein contains a matrix layer that initially is completely encapsulated by the top layer and bottom layer (in all three dimensions), and the dissolvable film is subsequently cut into a plurality of dosage strips. In such a scenario, the matrix layer may be enclosed by the top later and bottom layer in only two of the three physical dimensions (x and y axis), but not in the third dimension (the z axis, corresponding to the thickness of the dissolvable film). In such a scenario, the matrix layer is considered to be encapsulated by the top later and the bottom layer.

Alternatively, the dissolvable film can be manufactured such that there is an interface between each of the bottom-matrix layers and the top-matrix layers, and the interface is along at least two of the three physical dimensions, the length (x-axis) and the width (y-axis). In such a scenario, the matrix layer may be enclosed by the top later and bottom layer in two of the three physical dimensions (x and y axis), but not in the third dimension (the z axis, corresponding to the thickness of the dissolvable film). In such a scenario, the matrix layer is considered to be encapsulated by the top later and the bottom layer.

In the dissolvable films described herein, the active ingredient(s) can be encapsulated. For example, the active ingredient(s) can be encapsulated by cationic polymers and/or anionic polymers (e.g., polymers of dimethyl-aminoethyl-methacrylates, methacrylicacid, and methacrylic acid esters). Alternatively, the active ingredient(s) can be encapsulated with an emulsifier/plasticizer (e.g., glycerin). The active ingredient(s) can be partially (e.g., up to about 95 wt. %) or completely encapsulated.

The substances used to manufacture the dissolvable film can be selected in an amount such that a desired dissolution rate can be targeted. Upon contact with mucosal tissue (including, e.g., oral mucosa) the dissolvable film will completely dissolve within the desired period of time. The period of time will vary but in reference to the oral cavity, the period of time will typically be within about 30-300 seconds.

Dissolving films generally fall into three main classes: fast dissolving, moderate dissolving and slow dissolving. Fast dissolving films generally dissolve in about 1 second to about 60 seconds, with it typically being less than about 30 seconds. Moderate dissolving films generally dissolve in about 1 to about 30 minutes, and slow dissolving films generally dissolve in more than 30 minutes.

The dissolvable film can be manufactured in a manner, employing the ingredients described herein, such that any one or more of the desired pharmacokinetic metrics (e.g., dose, area under the curve, peak plasma concentration, dosing intervals, time to reach peak plasma concentration, clearance, bioavailability, etc.) are achieved. For example, the dissolvable film can be manufactured such that the dissolvable film provides for an immediate release (IR), controlled release (CR), modified release (MR), extended release (ER), or combination thereof, of active ingredient(s). This can be advantageous in those embodiments wherein multiple active ingredients are employed, each having different chemical and/or physical properties (e.g., pharmacokinetics, absorption kinetics, stability, solubility, bioavailability, etc.). The dissolvable films described herein therefore possess the potential to allow the development of drug targets that may otherwise not be feasible in tablet or liquid formulations (e.g., unpleasant taste and/or high dosage).

Kits

Pharmaceutical kits are also within the ambit of the present invention. Such kits include a therapeutically effective amount of a dissolvable film as described herein. Sterilization of the dissolvable film and/or packaging material may be carried out using conventional sterilization methodology well-known to those skilled in the art. Instructions or printed indicia, either as inserts or as labels, indicating quantities of the components to be administered, guidelines for administration, may also be included in the kit.

Utility

The dissolvable films described herein can be useful to deliver active ingredient(s) to the intended target. The dissolvable film can be placed, e.g., in the mouth thereby administering active ingredient(s) via absorption in the mouth (transmucosally, buccally or sublingually). Such a dissolvable film will be edible (suitable for human consumption), and pharmaceutically acceptable. The dissolvable films can be prepared typically using hydrophilic polymers that rapidly dissolve on the tongue or buccal cavity, delivering the active ingredient to the systemic circulation via dissolution when contact with liquid is made. The dissolvable film can also be used to adhere to mucosal tissue (e.g., mouth), thereby locally delivering the active ingredient(s) to that bodily tissue. As such, the mucoadhesive films may be used for the administration of active(s) to specific oral surfaces.

The dissolvable films may be applied under or to the tongue of the mammal. When this is desired, a specific film shape such as a square or rectangle, or a shape corresponding to the shape of the tongue, may be preferred. Therefore the film may be cut to a shape where the side of the film corresponding to the back of the tongue will be longer than the side corresponding to the front of the tongue. Specifically, the desired shape may be that of a triangle or trapezoid. Desirably, the dissolvable film will adhere to the oral cavity preventing it from being ejected from the oral cavity and permitting more of the active to be introduced to the oral cavity as the film dissolves.

Another use for the dissolvable films described herein takes advantage of the films' tendency to dissolve quickly when introduced to a liquid. Active ingredient(s) may be introduced to a liquid (or liquid containing substance) by preparing a film as described herein, introducing it to a liquid (or liquid containing substance), and allowing it to dissolve. This may be used either to prepare a liquid dosage form of active(s). This may also be used to flavor a beverage or food product, or to add active ingredient(s) to a beverage or food product.

Another use for the dissolvable films described herein takes advantage of the films' mucoadhesion properties. The dissolvable films may therefore be applied to any mucosal surface (e.g., eyes, ears, inside the nose, inside the mouth, lip, the urethral opening, and the anus). Specifically, the dissolvable films can be applied to: Bronchial mucosa and the lining of vocal folds, endometrium: the mucosa of the uterus, esophageal mucosa, gastric mucosa, intestinal mucosa, nasal mucosa, olfactory mucosa, oral mucosa, penile mucosa, vaginal mucosa, frenulum of tongue, tongue, anal canal, and/or palpebral conjunctiva.

Systems and methods in accordance with the present invention overcome the dosage limitations of film delivery of medication by forming both a base (bottom) layer and a top layer that encapsulates the matrix containing the active ingredient desired to be delivered. By providing both a top layer and a base layer, the structural integrity of the matrix carrying the active ingredient may be enhanced and maintained, thereby permitting much higher dosages than would otherwise be possible using a film delivery mechanism. For example, dosages of up to or exceeding 300 mg can be attained in a strip small enough to be easily administered to a patient using systems and methods in accordance with the present invention. Rather than being limited to an active/structural polymer ratio of approximately less than 30%, systems and methods in accordance with the present invention permit the fabrication of high-dosage films with an active/structural polymer ratio of about 60%-70%. In many examples in accordance to the present invention, a high-dosage film may dissolve within the mouth of a patient in less than one minute.

In examples in accordance with the present invention, one or more of the base (bottom) layer and top layer may be formulated possessing other desirable properties. For example, additions may be made to the base layer and/or top layer to enhance the flavor of the layer, to facilitate the mucoadhesion of the resulting film, or to otherwise make the resulting film attractive, durable, and/or palatable to a patient. In some examples, different properties may be desired for the base layer and the top layer, such as different flavor profiles, different physical strength, varying degrees of mucoadhesive, and/or different rates of dissolution in saliva.

FIG. 1 depicts a cross-section of a film 100 prepared in accordance with the present invention. A base (bottom) layer 120 and a top layer 130 may contain between them a matrix layer 110. Matrix layer 110 may include a dissolvable matrix containing within it at least one active ingredient molecule with desired medicinal properties. Due to the incorporation of a high number of active ingredient molecules within matrix layer 110, matrix layer may lack structural integrity sufficient to exist as a film without the support of base layer 110 and top layer 130, which physically engage matrix layer 110 and hold matrix layer 110 in place until one or both of base layer 120 and top layer 130 are dissolved. For example when administered to a patient the saliva present in the mouth of a patient may dissolve base layer 110 and/or matrix layer 120, thereby permitting the rapid dissolution and swallowing of matrix layer 110 and the active ingredient(s) incorporated therein.

Figure 2:
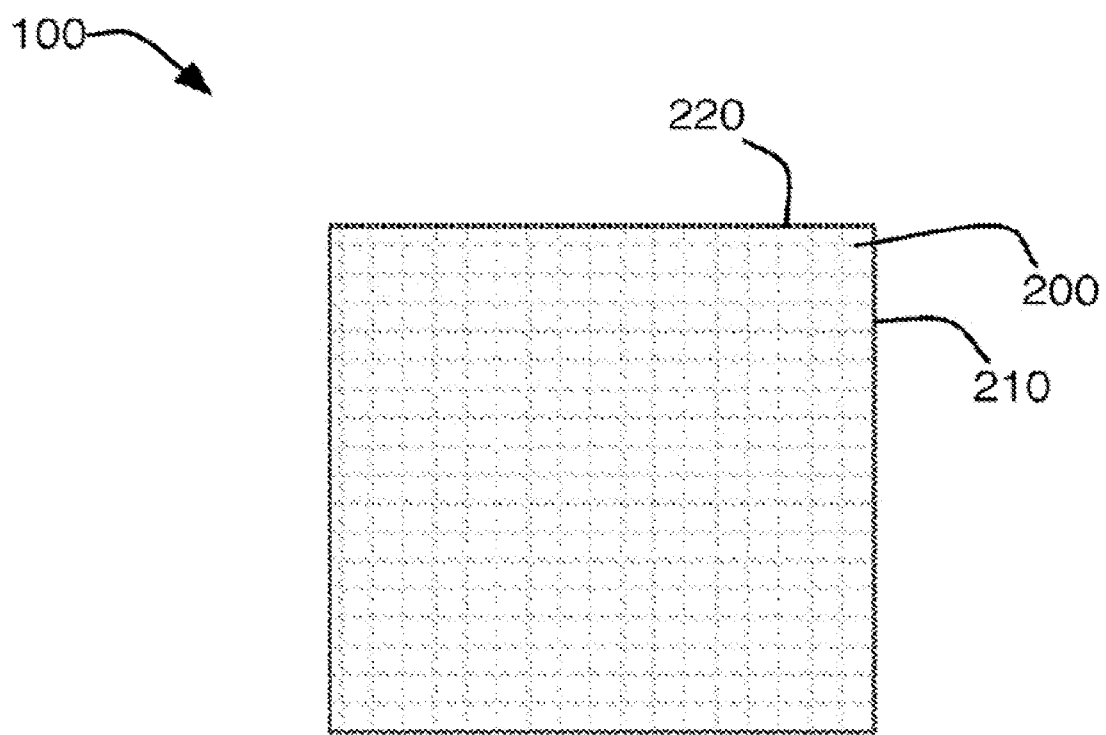
FIG. 2 illustrates a dissolvable film as described herein, configured to be cut into a plurality of dosage strips.

FIG. 2 illustrates a film 100 that is to be cut into a plurality of dosage strips. Dosage strips may be formed from film 100 by making a plurality of horizontal cuts 210 and a plurality of vertical cuts 220 to form squares or rectangles of the film 100 having known dimensions. If, as described in examples herein, the distribution of the active ingredient(s) within the matrix layer 110 are distributed evenly and possesses a uniform thickness, the area of the resulting strip(s) cut will therefore correspond to a known dosage of the desired active ingredient contained within matrix layer 110. The resulting independent dosages strips, such as strip 200, may be packaged for distribution as appropriate for storage and delivery.

The multilayered film may be cut to desired dosage units, such as squares, rectangles, or other shaped some portions of the larger multilayered film. By evenly distributing the active ingredient(s) in the active ingredient slurry and controlling the thickness of the active ingredient layer, the area of a dosage unit will control the dose of active ingredient contained within that portion of the film.

In addition to providing greater integrity to the active ingredient layer, the use of both a base (bottom) layer and a top layer permit different properties to be created on opposing sides of a medicated oral film. For example, the additives contained in the base layer may differ from those contained in the top layer in order to produce different properties. Additionally/alternatively, the thickness of the top layer and the base layer may differ to produce different properties. For example, one side of a high-dosage medicated strip in accordance with the present invention may be contain additives to make that side rapidly dissolve while the other side may contain additives to make that side mucoadhesive. In other examples, different flavor additives may be used in the top layer, base layer, and/or active ingredient layer to more effectively mask a distasteful medicine or to provide a more pleasing flavor profile. In some examples, different color additives may be included in the base layer than in the top layer, or a color additive may be added to only one of those layers, in order to permit a medical professional, a patient, and/or a caregiver to differentiate between the sides.

Systems and methods in accordance with the present invention may be used to deliver a wide variety of active ingredients to treat a patient's condition or symptoms. For example, high-dosage dissolvable strips in accordance with the present invention may be used in the treatment of infections, cardiac conditions, high cholesterol, migraines, insomnia, allergies, depression or bipolar disorders, and/or as diuretics, although other types of medications may additionally and/or alternatively delivered using high-dosage dissolvable strips in accordance with the present invention. Examples of anti-infective medications that may be administered using high-dosage strips in accordance with the present invention include, but are not limited to, Ciprofloxacin, Levofloxacin, Cephalexin, Amoxicillin, Metronidazole, Vancomycin, Clindamycin, and Metronidazole. Examples of cardiac medications that may be administered using high-dosage strips in accordance with the present invention include, but are not limited to, anticoagulants (such as Clopidogrel, Warfarin, Xarelto, Eliquis, etc.), beta blockers (such as Atenolol, Propranolol, Carvedilol, etc.), calcium channel blockers (such as Diltiazem, Verapamil, etc.), ACE inhibitors (such as Captopril, Enalapril, Lisinopril, Ramipril, etc.), ARBS (such as Losartan, Valsartan, Irbesartan, etc.), antiarrhythmic (such as Amiodarone, Sotalol, etc.), and DA vasodilators (such as Hydralazine, Nitroprusside, etc.). Examples of cholesterol lowering medications that may be administered using high-dosage strips in accordance with the present invention include, but are not limited to, Crestor, Atorvastatin, Simvastatin, Lovastatin, Pravastatin, and Zetia. Examples of migraine medications that may be administered using highdosage strips in accordance with the present invention include, but are not limited to, Sumatriptan, Topiramate, Zolmitriptan, and Rizatriptan. Examples of medications used to treat depression and/or bipolar disorder that may be administered using high-dosage strips in accordance with the present invention include, but are not limited to, Duloxetine, Oxazepam, Chlorpromazine, Bupropion, Venlafaxine, Amitriptyline, Nortriptyline, Aripiprazole, Carbamazepine, Lamotrigine, Quetiapine, Haloperidol, and Mirtazapine. Examples of medications used to treat migraines that may be administered using high-dosage strips in accordance with the present invention include, but are not limited to, Sumatriptan, Topiramate, Zolmitriptan, and Rizatriptan. Examples of sleep medications that may be administered using high-dosage strips in accordance with the present invention include, but are not limited to, Temazepam, Diphenhydramine, and Trazodone. Examples of diuretic medications that may be administered using high-dosage strips in accordance with the present invention include, but are not limited to, Furosemide, Hydrochlorothiazide, Torsemide, Spironolactone, and Indapamide. Examples of allergy medications that may be administered using high-dosage strips in accordance with the present invention include, but are not limited to, Meclizine, Loratadine, Cetirizine, Levocetirizine, and Montelukast.

Systems and methods in accordance with the present invention may enable the preparation of dissolvable films containing relatively high dosages of active ingredients for the oral treatment of patients. By containing the matrix incorporating the active ingredient between a base layer and a top layer, the structural and physical integrity of the film, and in particular the matrix layer carrying the active ingredient(s), may be maintained without having to keep the active ingredient loading ratio low, such as less than 30% by weight or less than 50% by weight, in order to avoid the disintegration of the structural polymer of the matrix layer. The high dosage films produced in accordance with the present invention may be useful in a number of clinical settings, such in the treatment of pediatric patients or geriatric patients who may have difficulty swallowing medicine in a pill form. Further, dosage strips in accordance with the present invention are resilient due to the formation of both a base layer and a top layer, thereby protecting the active layer from reacting with the environment or degrading due to physical handling. Especially in conjunction with protective packaging, high-dosage strips in accordance with the present invention may deliver easily administered, long-lasting medical dosages for a wide range of patients.

Methods of Manufacturing

The present invention provides for a method of manufacturing the oral dissolvable film described herein. The method can be carried out in any suitable manner and under any suitable conditions, provided the oral dissolvable film, as described herein, is obtained. In specific embodiments, the method is described below (illustrated in FIG. 3). Specifically, the method of manufacturing the oral dissolvable film can include: preparing a base material, spreading the base material in a solution on a carrier, drying the base material, preparing an active ingredient slurry, spreading the active ingredient slurry on the dried base material, drying the active layer, preparing the top material, spreading the top material on the dried active ingredient layer, drying the top layer, and curing the multi-layered oral dissolvable film.

Figure 3:
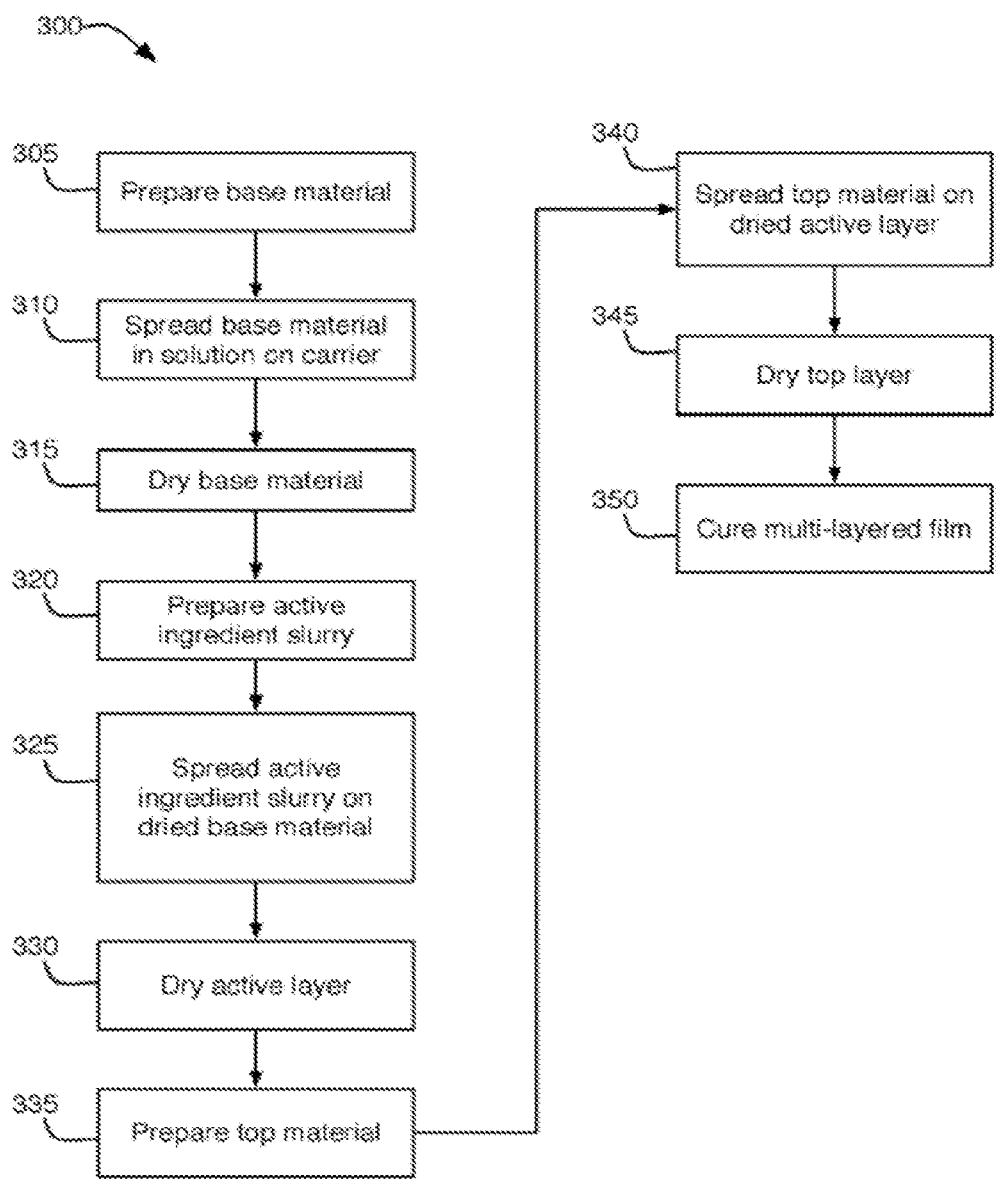
FIG. 3 illustrates a method of forming a dissolvable film as described herein.

Referring to FIG. 3, an exemplary method 300 of forming medicated films in accordance with the present invention is illustrated. In step 305 a base material may be prepared. Step 305 may include the preparation of a solution containing ingredients that will form a sturdy, thin membrane as well as providing desired properties such as flavor mucoadhesive, and other properties ultimately desired for the base layer. The base material may include a solubility agent (such as water, ethanol, etc.), flavoring(s) (such as orange, mint, vanilla, cherry, etc.), a lipid or emulsifier (such as glycerin, sorbitol, etc.), sweetener(s) (such as dextrose, sucrose, truvia, etc.), structural polymer(s) (such as carboxymethylcellulose, microcrystalline cellulose, pullulan, polyvinylpyrrolidone, pectin, etc.), and/or color agent(s). The combined ingredients may be mixed with a high shear mixer or folded together to uniformly disperse the component ingredients in the resulting solution.

In step 310 the base material may be spread while in solution onto a carrier. A carrier may include a sterile surface to retain the base material spread in a layer for further processing. Examples of carriers are tempered glass, siliconized paper, PET paper, etc. The base material may be extruded onto a carrier using the aperture of the extruder nozzle to control the thickness of the base material deposited. In other examples, the base material may be manually or mechanically spread to a desired thickness using a wire, stainless steel bar or other device to control the thickness of material deposited upon the carrier. In some examples, the thickness of the base material layer may range between 0.0126 inches (corresponding to a 28 gauge wire) to 0.20430 inches (corresponding to a 4 gauge wire). In step 315 the base material may be dried upon the carrier, for example through air drying, infrared drying, lyophilization, or drying in an oven.

In step 320 the active ingredient slurry may be prepared. The active ingredient slurry may include a solubility agent (such as water, ethanol, etc.), flavoring(s) (such as orange, mint, vanilla, cherry, etc.), a lipid or emulsifier (such as glycerin, sorbitol, etc.), sweetener(s) (such as dextrose, sucrose, truvia (stevia-based sugar substitute), etc.), structural polymer(s) (such as carboxymethylcellulose, microcrystalline cellulose, pullulan, polyvinylpyrrolidone, Kollicoat Protect, pectin, etc.), and/or color agent(s). The combined ingredients may be blended with a high shear mixer to evenly disperse the component ingredients in the resulting solution. An active ingredient(s) may be added to the solution at a desired dosage. Examples of active ingredients that may be added are isoniazid, amoxicillin, acetaminophen, diphenhydramine, aspirin and any other medicine that may be used orally. The active ingredient(s) may be incorporated into the mixture by applying high sheer or folding techniques for a time sufficient to insure the total and even distribution of the active ingredient throughout the mixture.

In step 325 the active ingredient slurry may be spread upon the dried base material after the completion of step 315. The active ingredient layer may be extruded onto the base layer using the aperture of the extruder nozzle to control the thickness of the base material deposited. In other examples, the active ingredient layer may be manually or mechanically spread to a desired thickness using a wire, stainless steel bar or other device to control the thickness of the active ingredient layer deposited upon the base layer. The active ingredient slurry may be spread to a desired thickness using a wire, stainless steel bar or other device to control the thickness of material deposited upon the base layer. In some examples, the thickness of the active ingredient layer may range between 0.0126 inches (corresponding to a 28 gauge wire) to 0.20430 inches (corresponding to a 4 gauge wire). In step 330 the active layer may be dried, for example through air drying, infrared drying, lyophilization, or drying in an oven.

In step 335, the top material may be prepared, such as by incorporating ingredients that will form an appropriately sturdy top layer and provide any desired flavoring, mucoadhesive, or other properties. The material prepared for the top layer in step 335 and the material prepared for base layer in step 305 may be the same or different and may provide different or the same properties. The top material may include a solubility agent (such as water, ethanol, etc.), flavoring(s) (such as orange, mint, vanilla, cherry, etc.), a lipid or emulsifier (such as glycerin, sorbitol, etc.), sweetener(s) (such as dextrose, sucrose, truvia, etc.), structural polymer(s) (such as carboxymethylcellulose, microcrystalline cellulose, pullulan, polyvinylpyrrolidone, Kollicoat Protect, pectin, etc.), and/or color agent(s). The combined ingredients may be mixed with a high shear mixture to evenly disperse the component ingredients in the resulting solution.

In step 340, the top material may be spread upon the dried active layer resulting from step 330. Step 340 may use a brush, roller, or other tool to evenly spread the top material. In some examples, the top layer may be extruded to a desired thickness and then applied to the active ingredient layer. In yet other examples, the top material may be extruded directly onto the active ingredient layer. In some examples, the thickness of the top material layer may range between 0.0126 inches (corresponding to a 28 gauge wire) to 0.20430 inches (corresponding to a 4 gauge wire). In step 345, the top layer may be dried, for example through air drying, infrared drying, lyophilization, or using an oven. In step 350, the resulting multilayered film may be cured for further processing.

Specific Ranges, Values, and Embodiments

In specific embodiments, the dissolvable film is an oral thin film (OTF).

In specific embodiments, the dissolvable film is an oral thin film (OTF), having a thickness of from about 0.10 mm to about 10 mm.

In specific embodiments, the dissolvable film is an oral thin film (OTF), having a thickness of about 0.20±0.10 mm.

In specific embodiments, the dissolvable film is an oral thin film (OTF), having a thickness of about 0.15±0.05 mm.

In specific embodiments, the dissolvable film is an oral thin film (OTF) configured to dissolve within about 60 seconds when placed in the mouth.

In specific embodiments, the dissolvable film is an oral thin film (OTF) configured to dissolve within about 45 seconds when placed in the mouth.

In specific embodiments, the dissolvable film is an oral thin film (OTF) configured to dissolve within about 30 seconds when placed in the mouth.

In specific embodiments, the top layer is substantially devoid of active pharmaceutical ingredient(s).

In specific embodiments, the top layer contains less than about 1 wt. % active pharmaceutical ingredient(s).

In specific embodiments, the top layer contains less than about 0.1 wt. % active pharmaceutical ingredient(s).

In specific embodiments, the top layer contains less than about 0.05 wt. % active pharmaceutical ingredient(s).

In specific embodiments, the top layer is substantially devoid of active pharmaceutical ingredient(s).

In specific embodiments, the top layer contains less than about 1 wt. % active pharmaceutical ingredient(s).

In specific embodiments, the top layer contains less than about 0.1 wt. % active pharmaceutical ingredient(s).

In specific embodiments, the top layer contains less than about 0.05 wt. % active pharmaceutical ingredient(s).

In specific embodiments, the top layer is mucoadhesive.

In specific embodiments, both the top layer and the top layer are mucoadhesive.

In specific embodiments, the top layer includes up to about 40 wt. % binders.

In specific embodiments, the top layer includes up to about 30 wt. % binders.

In specific embodiments, the top layer includes at least about 20 wt. % binders.

In specific embodiments, the top layer includes at least about 30 wt. % binders.

In specific embodiments, the top layer includes about 20 wt. % to about 40 wt. % binders.

In specific embodiments, the top layer includes about 25 wt. % to about 35 wt. % binders.

In specific embodiments, the top layer includes up to about 40 wt. % sweeteners.

In specific embodiments, the top layer includes up to about 30 wt. % sweeteners.

In specific embodiments, the top layer includes at least about 20 wt. % sweeteners.

In specific embodiments, the top layer includes at least about 30 wt. % sweeteners.

In specific embodiments, the top layer includes about 20 wt. % to about 40 wt. % sweeteners.

In specific embodiments, the top layer includes about 25 wt. % to about 35 wt. % sweeteners.

In specific embodiments, the top layer includes up to about 25 wt. % emulsifiers.

In specific embodiments, the top layer includes up to about 18 wt. % emulsifiers.

In specific embodiments, the top layer includes at least about 5 wt. % emulsifiers.

In specific embodiments, the top layer includes at least about 8 wt. % emulsifiers.

In specific embodiments, the top layer includes about 5 wt. % to about 25 wt. % emulsifiers.

In specific embodiments, the top layer includes about 8 wt. % to about 18 wt. % emulsifiers.

In specific embodiments, the top layer includes binders that provide tensile strength to top layer.

In specific embodiments, the top layer includes binders that provide mucosa adhesion to top layer.

In specific embodiments, the top layer includes binders that provide tensile strength and mucosa adhesion to top layer.

In specific embodiments, the matrix layer includes up to about 10 wt. % emulsifiers/surfactant.

In specific embodiments, the matrix layer includes up to about 5 wt. % emulsifiers/surfactant.

In specific embodiments, the matrix layer includes at least about 0.5 wt. % emulsifiers/surfactant.

In specific embodiments, the matrix layer includes at least about 1.5 wt. % emulsifiers/surfactant.

In specific embodiments, the matrix layer includes about 0.5 wt. % to about 10 wt. % emulsifiers/surfactant.

In specific embodiments, the matrix layer includes about 1.5 wt. % to about 5 wt. % emulsifiers/surfactant.

In specific embodiments, the matrix layer includes up to about 20 wt. % sweetener.

In specific embodiments, the matrix layer includes up to about 15 wt. % sweetener.

In specific embodiments, the matrix layer includes at least about 5 wt. % sweetener.

In specific embodiments, the matrix layer includes at least about 7.5 wt. % sweetener.

In specific embodiments, the matrix layer includes about 5 wt. % to about 20 wt. % sweetener.

In specific embodiments, the matrix layer includes about 7.5 wt. % to about 15 wt. % sweetener.

In specific embodiments, the matrix layer includes up to about 20 wt. % binder.

In specific embodiments, the matrix layer includes up to about 15 wt. % binder.

In specific embodiments, the matrix layer includes at least about 5 wt. % binder.

In specific embodiments, the matrix layer includes at least about 7.5 wt. % binder.

In specific embodiments, the matrix layer includes about 5 wt. % to about 20 wt. % binder.

In specific embodiments, the matrix layer includes about 7.5 wt. % to about 15 wt. % binder.

In specific embodiments, the matrix layer includes up to about 90 wt. % active ingredient(s).

In specific embodiments, the matrix layer includes up to about 85 wt. % active ingredient(s).

In specific embodiments, the matrix layer includes up to about 80 wt. % active ingredient(s).

In specific embodiments, the matrix layer includes up to about 75 wt. % active ingredient(s).

In specific embodiments, the matrix layer includes at least about 50 wt. % active ingredient(s).

In specific embodiments, the matrix layer includes at least about 60 wt. % active ingredient(s).

In specific embodiments, the matrix layer includes at least about 65 wt. % active ingredient(s).

In specific embodiments, the matrix layer includes at least about 70 wt. % active ingredient(s).

In specific embodiments, the matrix layer includes about 50 wt. % to about 90 wt. % active ingredient(s).

In specific embodiments, the matrix layer includes about 60 wt. % to about 90 wt. % active ingredient(s).

In specific embodiments, the matrix layer includes about 65 wt. % to about 90 wt. % active ingredient(s).

In specific embodiments, the matrix layer includes about 70 wt. % to about 90 wt. % active ingredient(s).

In specific embodiments, the matrix layer includes about 50 wt. % to about 80 wt. % active ingredient(s).

In specific embodiments, the matrix layer includes about 60 wt. % to about 80 wt. % active ingredient(s).

In specific embodiments, the matrix layer includes about 65 wt. % to about 80 wt. % active ingredient(s).

In specific embodiments, the matrix layer includes about 70 wt. % to about 80 wt. % active ingredient(s).

In specific embodiments, the matrix layer includes about 50 wt. % to about 75 wt. % active ingredient(s).

In specific embodiments, the matrix layer includes about 60 wt. % to about 75 wt. % active ingredient(s).

In specific embodiments, the matrix layer includes about 65 wt. % to about 75 wt. % active ingredient(s).

In specific embodiments, the matrix layer includes about 70 wt. % to about 75 wt. % active ingredient(s).

In specific embodiments, the matrix layer includes cationic polymers and/or anionic polymers, for encapsulating the active ingredient(s).

In specific embodiments, the matrix layer includes synthetic cationic polymers and/or synthetic anionic polymers, for encapsulating the active ingredient(s).

In specific embodiments, the active ingredient(s) are encapsulated with Eudragit® polymers (polymethacrylates).

In specific embodiments, the active ingredient(s) are encapsulated with cationic or anionic polymers.

In specific embodiments, the active ingredient(s) are encapsulated with synthetic cationic or anionic polymers of dimethyl-aminoethylmethacrylates, methacrylicacid, and methacrylic acid esters in varying ratios.

In specific embodiments, the active ingredient(s) are encapsulated with polymethacrylate polymers.

In specific embodiments, the active ingredient(s) are encapsulated with Eudragit® EPO (EE), a cationic polymer having a mean relative molecular mass of about 150,000, which prepared by copolymerization of butyl methacrylate, 2-dimethylaminoethylmethacrylate, and methyl methacrylate. The ratio of dimethylaminoethyl methacrylate groups to butyl methacrylate and methyl methacrylate groups is about 2:1:1.

In specific embodiments, the active ingredient(s) are encapsulated with Eudragit® L 100-55 (EL), an anionic copolymer based on methacrylic acid and ethylacrylate. The ratio of free carboxyl groups to the ester groups is approximately 1:1.

In specific embodiments, the active ingredient(s) are encapsulated with an emulsifier/plasticizer.

In specific embodiments, the active ingredient(s) are encapsulated with glycerin.

In specific embodiments, the active ingredient(s) are completely encapsulated.

In specific embodiments, up to about 95 wt. % of the active ingredient(s) are encapsulated.

In specific embodiments, up to about 90 wt. % of the active ingredient(s) are encapsulated.

In specific embodiments, up to about 80 wt. % of the active ingredient(s) are encapsulated.

In specific embodiments, up to about 70 wt. % of the active ingredient(s) are encapsulated.

In specific embodiments, up to about 60 wt. % of the active ingredient(s) are encapsulated.

In specific embodiments, up to about 50 wt. % of the active ingredient(s) are encapsulated.

In specific embodiments, up to about 40 wt. % of the active ingredient(s) are encapsulated.

In specific embodiments, up to about 30 wt. % of the active ingredient(s) are encapsulated.

In specific embodiments, up to about 20 wt. % of the active ingredient(s) are encapsulated.

In specific embodiments, at least about 5 wt. % of the active ingredient(s) are encapsulated.

In specific embodiments, at least about 10 wt. % of the active ingredient(s) are encapsulated.

In specific embodiments, at least about 15 wt. % of the active ingredient(s) are encapsulated.

In specific embodiments, at least about 20 wt. % of the active ingredient(s) are encapsulated.

In specific embodiments, at least about 25 wt. % of the active ingredient(s) are encapsulated.

In specific embodiments, at least about 30 wt. % of the active ingredient(s) are encapsulated.

In specific embodiments, at least about 40 wt. % of the active ingredient(s) are encapsulated.

In specific embodiments, at least about 50 wt. % of the active ingredient(s) are encapsulated.

In specific embodiments, at least about 60 wt. % of the active ingredient(s) are encapsulated.

In specific embodiments, at least about 70 wt. % of the active ingredient(s) are encapsulated.

In specific embodiments, at least about 80 wt. % of the active ingredient(s) are encapsulated.

In specific embodiments, at least about 90 wt. % of the active ingredient(s) are encapsulated.

In specific embodiments, about 5 wt. % to about 95 wt. % of the active ingredient(s) are encapsulated.

In specific embodiments, about 5 wt. % to about 90 wt. % of the active ingredient(s) are encapsulated.

In specific embodiments, about 5 wt. % to about 80 wt. % of the active ingredient(s) are encapsulated.

In specific embodiments, about 5 wt. % to about 70 wt. % of the active ingredient(s) are encapsulated.

In specific embodiments, about 5 wt. % to about 60 wt. % of the active ingredient(s) are encapsulated.

In specific embodiments, about 5 wt. % to about 50 wt. % of the active ingredient(s) are encapsulated.

In specific embodiments, about 5 wt. % to about 40 wt. % of the active ingredient(s) are encapsulated.

In specific embodiments, about 5 wt. % to about 30 wt. % of the active ingredient(s) are encapsulated.

In specific embodiments, about 5 wt. % to about 25 wt. % of the active ingredient(s) are encapsulated.

In specific embodiments, about 5 wt. % to about 20 wt. % of the active ingredient(s) are encapsulated.

In specific embodiments, about 5 wt. % to about 15 wt. % of the active ingredient(s) are encapsulated.

In specific embodiments, the matrix layer includes binders that provide tensile strength to matrix layer.

In specific embodiments, the active ingredient(s) include one or more cannabinoids.

In specific embodiments, the matrix layer includes binders that allow for rapid dissolution.

In specific embodiments, the matrix layer includes binders that provide tensile strength to matrix layer and allow for rapid dissolution of the matrix layer.

In specific embodiments, the top layer includes up to about 75 wt. % binders.

In specific embodiments, the top layer includes up to about 60 wt. % binders.

In specific embodiments, the top layer includes up to about 55 wt. % binders.

In specific embodiments, the top layer includes at least about 35 wt. % binders.

In specific embodiments, the top layer includes at least about 40 wt. % binders.

In specific embodiments, the top layer includes at least about 50 wt. % binders.

In specific embodiments, the top layer includes about 35 wt. % binders to about 75 wt. % binders.

In specific embodiments, the top layer includes about 40 wt. % binders to about 60 wt. % binders.

In specific embodiments, the top layer includes about 45 wt. % binders to about 60 wt. % binders.

In specific embodiments, the top layer includes about 40 wt. % binders to about 55 wt. % binders.

In specific embodiments, the top layer includes about 45 wt. % binders to about 55 wt. % binders.

In specific embodiments, the top layer includes up to about 15 wt. % emulsifiers/surfactant.

In specific embodiments, the top layer includes up to about 10 wt. % emulsifiers/surfactant.

In specific embodiments, the top layer includes at least about 2.5 wt. % emulsifiers/surfactant.

In specific embodiments, the top layer includes at least about 5 wt. % emulsifiers/surfactant.

In specific embodiments, the top layer includes about 2.5 wt. % to about 15 wt. % emulsifiers/surfactant.

In specific embodiments, the top layer includes about 2.5 wt. % to about 10 wt. % emulsifiers/surfactant.

In specific embodiments, the top layer includes about 5 wt. % to about 15 wt. % emulsifiers/surfactant.

In specific embodiments, the top layer includes about 5 wt. % to about 10 wt. % emulsifiers/surfactant.

In specific embodiments, the top layer includes binders that create a topcoat or barrier to the matrix layer.

In specific embodiments, the top layer includes binders that protect the active ingredient(s) against air, moisture, and/or water.

In specific embodiments, the top layer includes binders that allow the top layer to dissolve rapidly when placed in the mouth.

In specific embodiments, the top layer and the bottom layer contain between them the matrix layer, such that they encapsulate the matrix layer.

In specific embodiments, the top layer and the bottom layer contain between them the matrix layer, such that they partially encapsulate the matrix layer.

In specific embodiments, the top layer and the bottom layer contain between them the matrix layer, such that they completely encapsulate the matrix layer.

In specific embodiments, the dissolvable film contains a single active ingredient.

In specific embodiments, the dissolvable film contains multiple active ingredients.

In specific embodiments, the one or more active ingredients include electrolyte(s) (e.g., isotonic, hypertonic, or hypotonic).

In specific embodiments, the one or more active ingredients include electrolyte(s) containing the primary ion sodium ($Na^+$), potassium ($K^+$), calcium ($Ca^{2+}$), magnesium ($Mg^{2+}$), chloride ($Cl^-$), hydrogen phosphate ($HPO_4^{2-}$), and/or hydrogen carbonate ($HCO^{3-}$).

In specific embodiments, the one or more active ingredients include vitamin(s).

In specific embodiments, the one or more active ingredients include fat-soluble vitamin(s).

In specific embodiments, the one or more active ingredients include vitamin A, D, E, and/or K.

In specific embodiments, the one or more active ingredients include water-soluble vitamin(s).

In specific embodiments, the one or more active ingredients include vitamin B1, B2, B3, B5, B6, B7, B9, B12, and/or C.

In specific embodiments, the one or more active ingredients include anti-infective medication, cardiac medication, cholesterol lowering medication, migraine medication, medication used to treat depression and/or bipolar disorder, medication used to treat migraines, sleep medication, diuretic medication, anti-inflammatory medication, non-steroidal anti-inflammatory medication, allergy medication, and combinations thereof.

In specific embodiments, the one or more active ingredients include Isoniazid, Ibuprofen, Ciprofloxacin, Levofloxacin, Cephalexin, Amoxicillin, Metronidazole, Vancomycin, Clindamycin, Metronidazole, Clopidogrel, Warfarin, Xarelto, Eliquis, Atenolol, Propranolol, Carvedilol, Diltiazem, Verapamil, Captopril, Enalapril, Lisinopril, Ramipril, Losartan, Valsartan, Irbesartan, Amiodarone, Sotalol, Hydralazine, Nitroprusside, Crestor, Atorvastatin, Simvastatin, Lovastatin, Pravastatin, Zetia, Sumatriptan, Topiramate, Zolmitriptan, Rizatriptan, Duloxetine, Oxazepam, Chlorpromazine, Bupropion, Venlafaxine, Amitriptyline, Nortriptyline, Aripiprazole, Carbamazepine, Lamotrigine, Quetiapine, Haloperidol, Mirtazapine, Temazepam, Diphenhydramine, Trazodone, Furosemide, Hydrochlorothiazide, Torsemide, Spironolactone, Indapamide, Meclizine, Loratadine, Cetirizine, Levocetirizine, Montelukast, and combinations thereof.

In specific embodiments, the active ingredient(s) exist in the free acid or free base form.

In specific embodiments, the active ingredient(s) exist as a salt, with a pharmaceutically acceptable counterion.

In specific embodiments, the dissolvable film contains a relatively high load of active ingredient(s).

In specific embodiments, the active ingredient(s) are present in a total amount of at least about 30 wt. % of the dissolvable film.

In specific embodiments, the active ingredient(s) are present in a total amount of at least about 35 wt. % of the dissolvable film.

In specific embodiments, the active ingredient(s) are present in a total amount of at least about 40 wt. % of the dissolvable film.

In specific embodiments, the active ingredient(s) are present in a total amount of at least about 50 wt. % of the dissolvable film.

In specific embodiments, the active ingredient(s) are present in a total amount of at least about 60 wt. % of the dissolvable film.

In specific embodiments, the active ingredient(s) are present in a total amount of about 30 wt. % to about 65 wt. % of the dissolvable film.

In specific embodiments, the active ingredient(s) are present in a total amount of about 30 wt. % to about 60 wt. % of the dissolvable film.

In specific embodiments, the active ingredient(s) are present in a total amount of about 30 wt. % to about 55 wt. % of the dissolvable film.

In specific embodiments, the active ingredient(s) are present in a total amount of about 30 wt. % to about 50 wt. % of the dissolvable film.

In specific embodiments, the base layer includes lipid/emulsifier/plasticizer and binding agent.

In specific embodiments, the base layer includes glycerin, carboxymethylcellulose, Kollidon 90F, Pullulan, and/or hydroxypropyl cellulose.

In specific embodiments, the base layer includes glycerin and at least one of carboxymethylcellulose, Kollidon 90F, Pullulan, and hydroxypropyl cellulose.

In specific embodiments, the base layer includes lipid/emulsifier/plasticizer, binding agent, and optionally flavor and/or sweetener.

In specific embodiments, the matrix layer includes lipid/emulsifier/plasticizer, binding agent, and active ingredient.

In specific embodiments, the matrix layer includes glycerin, active ingredient and at least one of Kollicoat Protect, hydroxypropyl cellulose, hypromellose, microcrystalline cellulose, and Kollidon 90F.

In specific embodiments, the matrix layer includes lipid/emulsifier/plasticizer, binding agent, active ingredient, and optionally flavor and/or sweetener.

In specific embodiments, the bottom layer includes binding agent.

In specific embodiments, the bottom layer includes at least one of Kollicoat Protect and Kollidon 90F.

In specific embodiments, the multilayer configuration of the dissolvable film (e.g., the top layer and the bottom layer, containing between them the matrix layer) effectively provides for a dissolvable film that contains a high load of active ingredient(s) (e.g., present in a total amount of at least about 30 wt. % of the dissolvable film).

In specific embodiments, the multilayer configuration of the dissolvable film (e.g., the active ingredient present only in the matrix layer, and not in the top layer and/or bottom layer) effectively provides for a dissolvable film that contains a high load of active ingredient(s) (e.g., present in a total amount of at least about 30 wt. % of the dissolvable film).

In specific embodiments, the multilayer configuration of the dissolvable film (e.g., the top layer and the bottom layer, containing between them the matrix layer) effectively maintain the structural and physical integrity of the dissolvable film (e.g., each of the top layer, the matrix layer, and the bottom layer).

In specific embodiments, the multilayer configuration of the dissolvable film (e.g., the active ingredient present only in the matrix layer, and not in the top layer and/or bottom layer) effectively maintain the structural and physical integrity of the dissolvable film (e.g., each of the top layer, the matrix layer, and the bottom layer).

In specific embodiments, the multilayer configuration of the dissolvable film (e.g., the top layer and the bottom layer, containing between them the matrix layer) effectively provides for a dissolvable film wherein the structural and physical integrity of the dissolvable film (e.g., each of the top layer, the matrix layer, and the bottom layer) is effectively maintained.

In specific embodiments, the multilayer configuration of the dissolvable film (e.g., the active ingredient present only in the matrix layer, and not in the top layer and/or bottom layer) effectively provides for a dissolvable film wherein the structural and physical integrity of the dissolvable film (e.g., each of the top layer, the matrix layer, and the bottom layer) is effectively maintained.

In specific embodiments, the multilayer configuration of the dissolvable film (e.g., the top layer and the bottom layer, containing between them the matrix layer) provides for a dissolvable film in which the unpleasant taste of any active ingredient(s) is affectively masked.

In specific embodiments, the multilayer configuration of the dissolvable film (e.g., the active ingredient present only in the matrix layer, and not in the top layer and/or bottom layer) provides for a dissolvable film in which the unpleasant taste of any active ingredient(s) is affectively masked.

In specific embodiments, the multilayer configuration of the dissolvable film (e.g., the top layer and the bottom layer, containing between them the matrix layer) provides for a dissolvable film while maintaining the physical dimension of the dissolvable film, such that it is an oral thin film.

In specific embodiments, the multilayer configuration of the dissolvable film (e.g., the active ingredient present only in the matrix layer, and not in the top layer and/or bottom layer) provides for a dissolvable film while maintaining the physical dimension of the dissolvable film, such that it is an oral thin film.

In specific embodiments, the multilayer configuration of the dissolvable film (e.g., the top layer and the bottom layer, containing between them the matrix layer) provides for a dissolvable film while maintaining the physical dimension of the dissolvable film, such that it is an oral thin film that dissolves quickly when placed in the mouth (e.g., within about 45 seconds).

In specific embodiments, the multilayer configuration of the dissolvable film (e.g., the active ingredient present only in the matrix layer, and not in the top layer and/or bottom layer) provides for a dissolvable film while maintaining the physical dimension of the dissolvable film, such that it is an oral thin film that dissolves quickly when placed in the mouth (e.g., within about 45 seconds).

In specific embodiments, the multilayer configuration of the dissolvable film (e.g., the top layer and the bottom layer, containing between them the matrix layer) provides for a dissolvable film while maintaining the physical dimension of the dissolvable film, such that it is an oral thin film that possess the requisite pharmacokinetic metrics (e.g., peak plasma concentration after administration (Cmax), time to reach Cmax (tmax), area under the curve (AUC), bioavailability (BA), dose, etc.).

In specific embodiments, the multilayer configuration of the dissolvable film (e.g., the active ingredient present only in the matrix layer, and not in the top layer and/or bottom layer) provides for a dissolvable film while maintaining the physical dimension of the dissolvable film, such that it is an oral thin film that possess the requisite pharmacokinetic metrics (e.g., peak plasma concentration after administration (Cmax), time to reach Cmax (tmax), area under the curve (AUC), bioavailability (BA), dose, etc.).

In specific embodiments, the multilayer configuration of the dissolvable film (e.g., the top layer and the bottom layer, containing between them the matrix layer) effectively provides for a dissolvable film having the requisite mucoadhesiveness in the top layer and/or bottom layer.

In specific embodiments, the multilayer configuration of the dissolvable film (e.g., the active ingredient present only in the matrix layer, and not in the top layer and/or bottom layer) effectively provides for a dissolvable film having the requisite mucoadhesiveness in the top layer and/or bottom layer.

In specific embodiments, the multilayer configuration of the dissolvable film (e.g., the top layer and the bottom layer, containing between them the matrix layer) effectively protects the active ingredient(s) from reacting with one or more substances typically present in dissolvable films, which in specific embodiments of the present invention, are not located in the matrix layer, but are located in the top layer and/or bottom layer. These substances include, e.g., solubility agent, flavoring, lipid or emulsifier, sweetener, coloring agent, and/or structural polymers, such as carboxymethylcellulose, microcrystalline cellulose, pullulan, polyvinylpyrrolidone, Kollicoat® Protect (water-soluble Kollicoat® IR and polyvinyl alcohol), and pectin.

In specific embodiments, the multilayer configuration of the dissolvable film (e.g., the active ingredient present only in the matrix layer, and not in the top layer and/or bottom layer) effectively protects the active ingredient(s) from reacting with one or more substances typically present in dissolvable films, which in specific embodiments of the present invention, are not located in the matrix layer, but are located in the top layer and/or bottom layer. These substances include, e.g., solubility agent, flavoring, lipid or emulsifier, sweetener, coloring agent, and/or structural polymers, such as carboxymethylcellulose, microcrystalline cellulose, pullulan, polyvinylpyrrolidone, Kollicoat® Protect (water-soluble Kollicoat® IR and polyvinyl alcohol), and pectin.

In specific embodiments, the multilayer configuration of the dissolvable film (e.g., the top layer and the bottom layer, containing between them the matrix layer) effectively protects the active ingredient(s) from reacting with the environment (e.g., moisture, oxygen, and/or sunlight), or from degrading due to physical handling.

In specific embodiments, the multilayer configuration of the dissolvable film (e.g., the active ingredient present only in the matrix layer, and not in the top layer and/or bottom layer) effectively protects the active ingredient(s) from reacting with the environment (e.g., moisture, oxygen, and/or sunlight), or from degrading due to physical handling.

In specific embodiments, the multilayer configuration of the dissolvable film (e.g., the top layer and the bottom layer, containing between them the matrix layer) effectively provides for a dissolvable film that is suitable for buccal administration.

In specific embodiments, the multilayer configuration of the dissolvable film (e.g., the active ingredient present only in the matrix layer, and not in the top layer and/or bottom layer) effectively provides for a dissolvable film that is suitable for buccal administration.

In specific embodiments, the multilayer configuration of the dissolvable film (e.g., the top layer and the bottom layer, containing between them the matrix layer) effectively provides for a dissolvable film that is suitable for sublingual administration.

In specific embodiments, the multilayer configuration of the dissolvable film (e.g., the active ingredient present only in the matrix layer, and not in the top layer and/or bottom layer) effectively provides for a dissolvable film that is suitable for sublingual administration.

In specific embodiments, the top layer and the bottom layer include different substances.

In specific embodiments, the top layer and the bottom layer include the same substances.

In specific embodiments, the top layer and the bottom layer include the same substances, in differing amounts.

In specific embodiments, the top layer and the bottom layer include the same substances, in the same amounts.

In specific embodiments, the thickness of the top layer and the bottom layer differ.

In specific embodiments, the thickness of the top layer and the bottom layer are the same.

In specific embodiments, the lipid/emulsifier/plasticizer is glycerin.

Enumerated Embodiments

Specific enumerated embodiments [1] to [41] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] A dissolvable film suitable for oral administration, comprising:
 (a) a top layer,
 (b) a matrix layer comprising at least one active ingredient present in a total amount of at least about 30 wt. %, and
 (c) a bottom layer
wherein,
 the top layer and the bottom layer contain between them the matrix layer,
 each of the top layer, the matrix layer, and the bottom layer is dissolvable, and
 at least one of the top layer and the bottom layer comprises one or more structural polymers, such that the dissolvable film is mucoadhesive.

[2.] The dissolvable film of embodiment [1], which is an oral thin film wherein each of the matrix layer, the top layer and the bottom layer has a thickness of about 0.0126 inches to about 0.20430 inches.

[3.] The dissolvable film of any one of embodiments [1]-[2], wherein the top layer and the bottom layer maintain the structural and physical integrity of the matrix layer.

[4.] The dissolvable film of any one of embodiments [1]-[3], wherein the top layer and the bottom layer physically engage the matrix layer and hold the matrix layer intact until at least one of the top layer and the bottom layer is dissolved.

[5.] The dissolvable film of any one of embodiments [1] [4], wherein the top layer and the bottom layer physically engage the matrix layer thereby protecting the at least one active ingredient from reacting with the environment or degrading due to physical handling.

[6.] The dissolvable film of any one of embodiments [1]-[5], which dissolves within the mouth of a patient in less than about one minute.

[7.] The dissolvable film of any one of embodiments [1] [6], wherein the at least one active ingredient is evenly distributed within the matrix layer.

[8.] The dissolvable film of any one of embodiments [1]-[7], wherein the at least one active ingredient is distributed within the matrix layer such that the matrix layer possesses a uniform thickness.

[9.] The dissolvable film of any one of embodiments [1]-[8], wherein the top layer, the bottom layer, or combination thereof, comprises at least one of a solubility agent, flavoring, liquid emulsifier, sweetener, and coloring agent.

[10.] The dissolvable film of any one of embodiments [1]-[9], wherein the matrix layer comprises at least one of a solubility agent, flavoring, lipid or emulsifier, sweetener, structural polymer, and coloring agent.

[11.] The dissolvable film of any one of embodiments [1] [10], wherein the matrix layer has a thickness of about 0.0126 inches to about 0.20430 inches.

[12.] The dissolvable film of any one of embodiments [1]-[11], wherein the top layer has a thickness of about 0.0126 inches to about 0.20430 inches.

[13.] The dissolvable film of any one of embodiments [1]-[12], wherein the bottom layer has a thickness of about 0.0126 inches to about 0.20430 inches.

[14.] The dissolvable film of any one of embodiments [1]-[13], wherein the top layer and the bottom layer comprise different substances.

[15.] The dissolvable film of any one of embodiments [1]-[13], wherein the top layer and the bottom layer comprise the same substances.

[16.] The dissolvable film of any one of embodiments [1]-[15], wherein the thickness of the top layer and the bottom layer differ.

[17.] The dissolvable film of any one of embodiments [1]-[16], wherein the matrix layer comprises at least one active ingredient present in a total amount of at least about 50 wt. % of the dissolvable film.

[18.] The dissolvable film of any one of embodiments [1]-[17], wherein the at least one active ingredient is selected from the group consisting of an anti-infective medication, cardiac medication, cholesterol lowering medication, migraine medication, medication used to treat depression and/or bipolar disorder, medication used to treat migraines, sleep medication, diuretic medication, anti-inflammatory medication, nonsteroidal anti-inflammatory medication, allergy medication, and combinations thereof.

[19.] The dissolvable film of any one of embodiments [1]-[18], wherein the at least one active ingredient is selected from the group consisting of Isoniazid, Ibuprofen, Ciprofloxacin, Levofloxacin, Cephalexin, Amoxicillin, Metronidazole, Vancomycin, Clindamycin, Metronidazole, Clopidogrel, Warfarin, Xarelto, Eliquis, Atenolol, Propranolol, Carvedilol, Diltiazem, Verapamil, Captopril, Enalapril, Lisinopril, Ramipril, Losartan, Valsartan, Irbesartan, Amiodarone, Sotalol, Hydralazine, Nitroprusside, Crestor, Atorvastatin, Simvastatin, Lovastatin, Pravastatin, Zetia, Sumatriptan, Topiramate, Zolmitriptan, Rizatriptan, Duloxetine, Oxazepam, Chlorpromazine, Bupropion, Venlafaxine, Amitriptyline, Nortriptyline, Aripiprazole, Carbamazepine, Lamotrigine, Quetiapine, Haloperidol, Mirtazapine, Temazepam, Diphenhydramine, Trazodone, Furosemide, Hydrochlorothiazide, Torsemide, Spironolactone, Indapamide, Meclizine, Loratadine, Cetirizine, Levocetirizine, Montelukast, and combinations thereof.

[20.] The dissolvable film of any one of embodiments [1]-[19], wherein the at least one active ingredient present in a total amount of at least about 300 mg.

[21.] The dissolvable film of any one of embodiments [1]-[20], wherein the one or more structural polymers comprise carboxymethyl cellulose, microcrystalline cellulose, pullulan, polyvinylpyrrolidone, Kollicoat® Protect (water-soluble Kollicoat® IR and polyvinyl alcohol), pectin, or a combination thereof.

[22.] A dissolvable film suitable for oral administration, comprising:
(a) a top layer comprising lipid, binding agent, and optionally flavor and/or sweetener,
(b) a matrix layer comprising lipid/emulsifier/plasticizer, binding agent, at least one active ingredient, and optionally flavor and/or sweetener, and
(c) a bottom layer comprising binding agent,
wherein,
the top layer and the bottom layer contain between them the matrix layer,
each of the top layer, the matrix layer, and the bottom layer is dissolvable, and the dissolvable film is mucoadhesive.

[23.] The dissolvable film of embodiment [22], wherein the at least one active ingredient is present in a total amount of at least about 30 wt. % of the dissolvable film.

[24.] A dissolvable film suitable for oral administration, comprising:
(a) a top layer comprising glycerin and at least one of carboxymethylcellulose, Kollidon 90F, Pullulan, hydroxypropyl cellulose, and optionally flavor and/or sweetener,
(b) a matrix layer comprising glycerin, active ingredient, and at least one of Kollicoat Protect, hydroxypropyl cellulose, hypromellose, microcrystalline cellulose, Kollidon 90F, and optionally flavor and/or sweetener, and
(c) a bottom layer comprising binding agent,
wherein,
the top layer and the bottom layer contain between them the matrix layer,
each of the top layer, the matrix layer, and the bottom layer is dissolvable, and the dissolvable film is mucoadhesive.

[25.] The dissolvable film of embodiment [24], wherein the at least one active ingredient is present in a total amount of at least about 30 wt. % of the dissolvable film.

[26.] The dissolvable film of any one of embodiments [24]-[25], wherein the bottom layer comprises at least one of Kollicoat Protect and Kollidon 90F.

[27.] The dissolvable film of any one of embodiments [24]-[25], wherein the bottom layer comprises at least one of about 10-30 mg Kollicoat Protect and about 4-15 mg Kollidon 90F.

[28.] The dissolvable film of any one of embodiments [24]-[25], wherein the bottom layer comprises at least one of about 20-24 mg Kollicoat Protect and about 8-10 mg Kollidon 90F.

[29.] The dissolvable film of any one of embodiments [24]-[28], wherein the matrix layer comprises one or more active ingredients in a total amount of about 200-650 mg.

[30.] The dissolvable film of any one of embodiments [24]-[28], wherein the matrix layer comprises one or more active ingredients in a total amount of about 250-650 mg.

[31.] The dissolvable film of any one of embodiments [24]-[30], wherein the matrix layer comprises glycerin.

[32.] The dissolvable film of any one of embodiments [24]-[30], wherein the matrix layer comprises glycerin in about 5-75 mg.

[33.] The dissolvable film of any one of embodiments [24]-[30], wherein the matrix layer comprises glycerin in about 11-53 mg.

[34.] The dissolvable film of any one of embodiments [24]-[33], wherein the matrix layer comprises at least one of Kollicoat Protect, hydroxypropyl cellulose, hypromellose, microcrystalline cellulose, and Kollidon 90F.

[35.] The dissolvable film of any one of embodiments [24]-[33], wherein the matrix layer comprises about 10-50 mg Kollicoat Protect, about 3-45 mg hydroxypropyl cellulose, about 2-10 mg hypromellose, about 3-35 mg microcrystalline cellulose, and about 0.5-10 mg Kollidon 90F.

[36.] The dissolvable film of any one of embodiments [24]-[33], wherein the matrix layer comprises about 19-37 mg Kollicoat Protect, about 6-34 mg hydroxypropyl cellulose, about 4-5 mg hypromellose, about 6-22 mg microcrystalline cellulose, and about 1-6 mg Kollidon 90F.

[37.] The dissolvable film of any one of embodiments [24]-[36], wherein the top layer comprises glycerin and at least one of 10-45 mg carboxymethylcellulose, 1-8 mg Kollidon 90F, 1-10 mg Pullulan, and 2-15 mg hydroxypropyl cellulose.

[38.] The dissolvable film of any one of embodiments [24]-[36], wherein the top layer comprises glycerin and at least one of 17-30 mg carboxymethylcellulose, 2-4 mg Kollidon 90F, 3-4 mg Pullulan, and 5-6 mg hydroxypropyl cellulose.

[39.] A dissolvable film suitable for oral administration, comprising:
(a) a top layer comprising lipid, binding agent, and optionally flavor and/or sweetener, and
(b) a matrix layer comprising lipid/emulsifier/plasticizer, binding agent, at least one active ingredient, and optionally flavor and/or sweetener,
wherein,
the top layer contacts the matrix layer,
each of the matrix layer and the top layer is dissolvable, and the dissolvable film is mucoadhesive.

[40.] The dissolvable film of embodiment [39], wherein the at least one active ingredient is present in a total amount of at least about 30 wt. % of the dissolvable film.

[41.] The dissolvable film of any one of embodiments [39]-[40], wherein the matrix layer comprises one or more active ingredients in a total amount of about 150-650 mg.

[42.] The dissolvable film of any one of embodiments [39]-[40], wherein the matrix layer comprises one or more active ingredients in a total amount of about 200-650 mg.

[43.] The dissolvable film of any one of embodiments [39]-[40], wherein the matrix layer comprises glycerin.

[44.] The dissolvable film of any one of embodiments [39]-[40], wherein the matrix layer comprises glycerin in about 15-75 mg.

[45.] The dissolvable film of any one of embodiments [39]-[40], wherein the matrix layer comprises glycerin in about 20-35 mg.

[46.] The dissolvable film of any one of embodiments [39]-[40], wherein the matrix layer comprises at least one of glycerin, carboxymethylcellulose, and Kollidon 90F.

[47.] The dissolvable film of any one of embodiments [39]-[40], wherein the matrix layer comprises about 20-45 mg glycerin, about 30-55 mg carboxymethylcellulose, and about 15-35 mg Kollidon 90F.

[48.] The dissolvable film of any one of embodiments [39]-[40], wherein the matrix layer comprises about 20-35 mg glycerin, about 35-50 mg carboxymethylcellulose, and about 15-30 mg Kollidon 90F.

[49.] The dissolvable film of any one of embodiments [39]-[48], wherein the top layer comprises glycerin, Kolidon 90F, and carb oxymethyl cellulose.

[50.] The dissolvable film of any one of embodiments [39] [48], wherein the top layer comprises about 20-40 mg glycerin, about 35-55 mg Kolidon 90F, and about 10-30 mg carboxymethylcellulose.

[51.] The dissolvable film of any one of embodiments [39]-[48], wherein the top layer comprises about 25-35 mg glycerin, about 40-50 mg Kolidon 90F, and about 15-25 mg carboxymethylcellulose.

[52.] A method comprising administering the dissolvable film of any one of embodiments [1]-[51], to a patient in need thereof, in an amount and for a period of time, effective to treat the patient's condition or symptom.

[53.] The method of embodiment [52], wherein the dissolvable film is administered for the treatment of an infection, cardiac condition, inflammation, high cholesterol, migraine, insomnia, allergies, depression or bipolar disorder, and/or as a diuretic.

[54.] The method of embodiment [52], wherein the route of administration is sublingual or transmucosal.

The invention can be further described with the following non-limiting examples.

EXAMPLES

Example 1: Preparation of Multi-Layered Dissolvable Film with High Drug Load A. Preparation of the base layer:

Weigh out the require amount of each of the sweeteners, emulsifiers, flavors, and water. The water used is deionized water at 60° C. Place into a 500 mL, then high shear the solution to mix the ingredients together. Mix for 1-2 mins.

Next weight each of binders into separate plastic weight boats. Once weighed, start adding the binder in the order or lowest quantity to highest. While adding the binders to the mixture, continuously high shear the solution to prevent agglomeration of binder particles. High shear the slurry for 5-10 mins to everything has gone into solution. Note, if the solution starts to becomes very thick add more deionized (DI) water at 60° C. until the desired consistency is achieved for making strips.

Then, take the newly mixed base layer slurry and place on the overhead stirrer and mix at 450-1100 rpm. Using a fan like mixer, allow the base layer to mix for 30-40 mins. By allowing the slurry to mix this vents the air bubbles from the slurry, which otherwise cause points of weakness within the strip. Note, if the solution starts to becomes very thick add more DI water at 60° C. until the desired consistency is found for making strips. If there are air bubbles remaining in the slurry, slow the mixing to 200-450 rpm and continue to mix this for another 20-30 mins.

After the duration of mixing on the overhead mixer, the slurry should be ready to spread the base layer on the glass. Spread the base slurry onto glass or PET, use a 20-gauge wire on the stainless steel bar. Place in the convection oven at a temperature of 80° C. for 18-22 mins.

At the half way point (around 9-12 mins) turn the glass to prevent one side of film from getting too dry. Remove the base layer when the film is slightly tacky (just enough tackiness "to leave a slight finger print indention on the strip"). Next, allow to cool. While cooling, start the preparation of the active (matrix) layer.

B. Preparation of Matrix ("Active") Layer:

Weigh out the require amounts of each of the sweeteners, emulsifiers, flavors, and water. The water use is deionized water at 60° C. Place into a 500 mL, then high shear the solution to mix the ingredients together. Mix for 1-2 mins. Note, water at 60° C. is fine to use with the everything in strip until the point of adding the API. At this point, any water added should take in consideration of API melting point to prevent decomposition of compound.

Weight each of binders into separate plastic weight boats. Once weighed, start adding the binder in the order or lowest quantity to highest. While adding the binders to mixture, continuously high shear the solution to prevent agglomeration of binder particles. High shear the slurry for 5-10 mins to everything has gone into solution. Then, take the newly mixed base layer slurry and place on the overhead stirrer and mix at 250-500 rpm. Using a fan like mixer, allow the base layer to mix for 5-10 mins.

While the active slurry is mixing, weigh out the API into a beaker or weigh boat. Note, use a sieve to insure that the API mesh size is equal and there are no large particle sizes that will cause problems with spreading the slurry by causing streaks on the strip.

After weighing/checking particle size of the API, start adding it to slurry that is mixing at 250-500 rpm. Add the API slowly to allow for even distribution of the API throughout the slurry. If the slurry starts to thicken add deionized water to thin the slurry. Then let mix for 20-30 mins at 150-450 rpm Once the slurry has mixed for 20-30 min, remove the slurry from the overhead stirrer. When the slurry is removed from the stirrer, pour the slurry onto the previously made base layer. Then spread the slurry using a 13-gauge wire on the bar. After the slurry has been spread place under the IR lamp, this will take 10-25 mins. The slurry needs to be rotated occasional about every 5-10 mins. Then, pull out of the oven once it has formed a dried film.

C. Preparation of Top ("Topcoat") Layer

Weigh out the require amounts of each of the water/ethanol, emulsifiers/surfactants, and binders. The water use is deionized water at 60° C. Place into a 500 mL then high shear the solution to mix the ingredients together. Mix for 1-2 mins. This slurry can froth up, so watch for excess frothing of the slurry.

Next, take the slurry and add to spray gun to spray the slurry on the previously dried active layer. Spray gun: settings 60-80 psi on the pneumatic spray tool.

Spray the previous dried active layer, to ensure the active layer is evenly coated with the topcoat. Then place in the IR oven for 2-5 mins, then remove with strip top layer is no longer sticky or tacky. Then, respray the strip again and repeat this process for a total of 4 times. Then, let the strip sit for 10-20 min then cut for packaging.

Example 2: Active Ingredient Encapsulation

Isoniazid (INH) Encapsulation:

Start out with the amount of the compound INH that you want to encapsulate. A 15% theoretical encapsulation has turned out to provide an actual 7% to 12% encapsulation.

Weigh out the amount of Eudragit EPO require to do the particular batch of INH Encapsulation. For example, if you're doing 50 g INH you need 7.5 of Eudragit EPO, and that needs to be dissolved into 200 mL of ethanol. To keep the mixture highly soluble, a 1:4 ratio of ethanol to grams of drug should be employed.

Once the Eudragit EPO is added to 200 proof Ethanol solvent, place under overhead and using a high shear blade, stir for 1.5 hours @ 600-800 rpms, then for last 0.5 hour, slow the stirrer to 180-300 rpm to allow any air bubbles to escape the solution.

During this 2 hour gap you can start grinding the INH powder with a coffee grinder to produce the smallest particle size feasible before adding to solution.

Once air bubbles have been removed from the Eudragit EPO solution, slowly increase the rpms to 500 rpms. Then start to slowly add the recently ground INH particles to the solution. If the mixture starts to get to viscous "more than a water consistency" add more ethanol. INH is only slightly soluble in Ethanol so you should see suspension. Let this mix for 20-40 mins Next, set up a vacuum filter to remove extra amounts of solvent from the mixture. After the mixing time has elapsed start slowly adding the solution to vacuum filter, allow the vacuum to pull off only enough of the solvent to create "wet clay like texture of compound/EPO Product".

While the vacuum filter is pulling off the solvent, set up the resuspension process. Using a 1000-1800 mL beaker add about 400-500 mL of hexane. Using the overhead stirrer place the rpms at 900-1500 rpm with a high shearing blade. In this solvent both INH and EPO will precipitate out and be suspended in the solution. Once the INH/EPO has reached the clay like texture start adding the INH/EPO filter compound to hexane solvent. Let the high shear to mix for 10-12 mins.

Using a 1000 mL round bottom flask start adding hexane/(INH/EPO) suspension to the flask using a funnel then place round bottom on roto-vap.

Using roto-vap settings: water bath: 60° C., round bottom revolution: 40-60 rpms, Vacuum pump: 340 atm.

At this setting the hexane should be boiling but not a boil that causes bumping of the solvent but a percolation enough to keep (INH/EPO) particles from agglomerating together in massive chunks. Once all the hexane solvent has been removed, lower the pressure to 165 atm to remove some of the ethanol from particles.

Watch carefully, and pull the round bottom flask off once the compound has reached a somewhat "dry doughy consistency".

When this consistency has been reached, pull the compound off the roto-vap then using a sieve and collection pan, add the compound to sieve and push the compound through to create an even mesh of the product. Then place in a preheated oven at 50° C. for 5 mins, to harden the INH/EPO particles.

After the 5 mins has elapse collect the particles and place back into the 1000 mL round bottom flask, and place back on roto-vap.

Using roto-vap settings: water bath: 60° C., round bottom revolution: 80-100 rpms, Vacuum pump: 100 atm. To pull as much of any remnants of hexane/ethanol within the particles.

While this is going on, the roto-vap you should be able to see the fine particle mesh folding over itself continuously throughout the revolutions. Keep this on the roto-vap for 1-2 hours to ensure that all of hazardous solvents have been removed.

Example 3: Multi-Layered Dissolvable Film with High Drug Load, Isoniazid 300 mg

| Layer of dissolvable film | Ingredient (amount) | Function |
|---|---|---|
| Top Layer: | Glycerin (11 mg) | Lipid/Emulsifier/Plasticizer |
| | Carboxymethyl cellulose (18 mg) | Binding Agent |
| | Kollidon 90F (2 mg) | Binding Agent |
| | Pullulan (3.16 mg) | Binding Agent |
| | Watkins Orange (1 mg) | Flavoring agent (optional) |
| | Virginia Dare Orange (2 mg) | Flavoring agent (optional) |
| | Citric Acid (1 mg) | Excipient (optional) |
| | Sucralose (3 mg) | Sweetener (optional) |
| | Magna Sweet 100 mm (0.8 mg) | Sweetener (optional) |
| | Acesulfame potassium (7 mg) | Sweetener (optional) |
| | Dextrose (3 mg) | Sweetener (optional) |
| Matrix (Active) Layer: | Glycerin (11 mg) | Lipid/Emulsifier/Plasticizer |
| | Kollicoat Protect (19.3 mg) | Binding Agent |
| | Hydroxypropyl Cellulose (16.1 mg) | Binding Agent |
| | Microcrystalline cellulose (8 mg) | Binding Agent |
| | Kollidon 90F (1.6 mg) | Binding Agent |
| | Isoniazid (300 mg) | Active Ingredient |
| | Watkins Orange (12 mg) | Flavoring agent (optional) |
| | Watkins Dare Cream (3 mg) | Flavoring agent (optional) |
| | Virginia Dare Orange (4 mg) | Flavoring agent (optional) |
| | Citric Acid (2 mg) | Excipient (optional) |
| | Creamer (2 mg) | Sweetener (optional) |
| | Honey (10 mg) | Sweetener (optional) |
| | Sucralose (5 mg) | Sweetener (optional) |
| | Acesulfame potassium (4 mg) | Sweetener (optional) |
| | Magna Sweet 100 mm (1.8 mg) | Sweetener (optional) |
| Bottom Layer: | Kollicoat Protect (21.7 mg) | Binding Agent |
| | Kollidon 90F (8.68 mg) | Binding Agent |

Example 4: Multi-Layered Dissolvable Film with High Drug Load, Ibuprofen 200 mg

| Layer of dissolvable film | Ingredient (amount) | Function |
|---|---|---|
| Top Layer: | Glycerin (8 mg) | Lipid/Emulsifier/Plasticizer |
| | Carboxymethylcellulose (17.6 mg) | Binding Agent |
| | Kollidon 90F (2.2 mg) | Binding Agent |
| | Pullulan (3.0 mg) | Binding Agent |
| | Watkins Lemon (10 mg) | Flavoring agent (optional) |
| | Citric Acid (2 mg) | Excipient (optional) |
| | Sucralose (13 mg) | Sweetener (optional) |
| | Acesulfame potassium (7 mg) | Sweetener (optional) |
| | Magna Sweet 100 mm (8 mg) | Sweetener (optional) |
| | Dextrose (3 mg) | Sweetener (optional) |
| Matrix (Active) Layer: | Glycerin (13.3 mg) | Lipid/Emulsifier/Plasticizer |
| | Kollicoat Protect (20 mg) | Binding Agent |
| | Hydroxypropyl Cellulose (6.6 mg) | Binding Agent |
| | Hypromellose (4.7 mg) | Binding Agent |
| | Microcrystalline cellulose (6.7 mg) | Binding Agent |

-continued

| Layer of dissolvable film | Ingredient (amount) | Function |
|---|---|---|
| | Kollidon 90F (1.3 mg) | Binding Agent |
| | Ibuprofen (200 mg) | Active Ingredient |
| | Lemon (18 mg) | Flavoring agent (optional) |
| | VD Lemon (6 mg) | Flavoring agent (optional) |
| | Citric Acid (2 mg) | Excipient (optional) |
| | Creamer (2 mg) | Sweetener (optional) |
| | Sucralose (8 mg) | Sweetener (optional) |
| | Acesulfame potassium (4 mg) | Sweetener (optional) |
| | Dextrose (8 mg) | Sweetener (optional) |
| Bottom Layer: | Kollicoat Protect (21.7 mg) | Binding Agent |
| | Kollidon 90F (8.7 mg) | Binding Agent |

Example 5: Multi-Layered Dissolvable Film with High Drug Load, Electrolytes 622 mg

| Layer of dissolvable film | Ingredient (amount) | Function |
|---|---|---|
| Top Layer: | Glycerin (17.7 mg) | Lipid/Emulsifier/Plasticizer |
| | Carboxymethylcellulose (29.45 mg) | Binding Agent |
| | Kollidon 90F (3.68 mg) | Binding Agent |
| | Hydroxypropyl Cellulose (5.2 mg) | Binding Agent |
| | Watkins Lemon (20 mg) | Flavoring agent (optional) |
| | Citric Acid (2 mg) | Excipient |
| | Sucralose (13 mg) | Sweetener (optional) |
| | Dextrose (12 mg) | Sweetener (optional) |
| Matrix (Active) Layer: | Glycerin (52.6 mg) | Lipid/Emulsifier/Plasticizer |
| | Kollicoat Protect (33 mg) | Binding Agent |
| | Microcrystalline cellulose (16.4 mg) | Binding Agent |
| | Potassium Chloride (98.68 mg) | Active Ingredient |
| | Potassium Citrate (98.68 mg) | Active Ingredient |
| | Sodium Chloride (98.68 mg) | Active Ingredient |
| | Sodium Citrate (260 mg) | Active Ingredient |
| | Zinc Gluconate (65.99 mg) | Active Ingredient |
| | Creamer (3 mg) | Excipient (optional) |
| | Citric Acid (0.8 mg) | Excipient (optional) |
| | Sucralose (6 mg) | Sweetener (optional) |
| | Dextrose (25 mg) | Sweetener (optional) |
| Bottom Layer: | Kollicoat Protect (20 mg) | Binding Agent |
| | Kollidon 90F ( 8 mg) | Binding Agent |

Example 6: Multi-Layered Dissolvable Film with High Drug Load, Acetaminophen 325 mg

| Layer of dissolvable film | Ingredient (amount) | Function |
|---|---|---|
| Top Layer: | Glycerin (8 mg) | Lipid/Emulsifier/Plasticizer |
| | Carboxymethylcellulose (20 mg) | Binding Agent |
| | Kollidon 90F (2.5 mg) | Binding Agent |
| | Pullulan (3.5 mg) | Binding Agent |
| | Watkins Lemon (9 mg) | Flavoring agent (optional) |
| | Virginia Dare Lemon (6 mg) | Flavoring agent (optional) |
| | Citric Acid (1 mg) | Excipient (optional) |
| | Sucralose (3 mg) | Sweetener (optional) |
| | Magna Sweet 100 mm (0.8 mg) | Sweetener (optional) |
| | Dextrose (1 mg) | Sweetener (optional) |
| Matrix (Active) Layer: | Glycerin (18 mg) | Lipid/Emulsifier/Plasticizer |
| | Kollicoat Protect (36.8 mg) | Binding Agent |
| | Hydroxypropyl Cellulose (34 mg) | Binding Agent |
| | Microcrystalline cellulose (21.1 mg) | Binding Agent |
| | Kollidon 90F (5.3 mg) | Binding Agent |
| | Acetaminophen (120 mg) | Active Ingredient |
| | Watkins Lemon (12 mg) | Flavoring agent (optional) |
| | Virginia Dare Cream (3 mg) | Flavoring agent (optional) |
| | Virginia Dare Lemon (4 mg) | Flavoring agent (optional) |
| | Citric Acid (3 mg) | Excipient (optional) |
| | Creamer (2 mg) | Sweetener (optional) |
| | Honey (10 mg) | Sweetener (optional) |
| | Sucralose (5 mg) | Sweetener (optional) |
| | Acesulfame potassium (4 mg) | Sweetener (optional) |
| | Magna Sweet 100 mm (1.8 mg) | Sweetener (optional) |
| Bottom Layer: | Kollicoat Protect (24 mg) | Binding Agent |
| | Kollidon 90F (10 mg) | Binding Agent |

Example 7: Multi-Layered Dissolvable Film with High Drug Load, Keflex 250 mg

| Layer of dissolvable film | Ingredient (amount) | Function |
|---|---|---|
| Top Layer: | Glycerin (8 mg) | Lipid/Emulsifier/Plasticizer |
| | Carboxymethylcellulose (21 mg) | Binding Agent |
| | Kollidon 90F (3 mg) | Binding Agent |
| | Pullulan (4 mg) | Binding Agent |
| | Watkins Mint (9 mg) | Flavoring agent (optional) |
| | Virginia Dare Spearmint (6 mg) | Flavoring agent (optional) |
| | Menthol (11 mg) | Excipient (optional) |
| | Sucralose (3 mg) | Sweetener (optional) |
| | Magna Sweet 100 mm (0.8 mg) | Sweetener (optional) |
| | Dextrose (2 mg) | Sweetener (optional) |
| Matrix (Active) Layer: | Glycerin (18 mg) | Lipid/Emulsifier/Plasticizer |
| | Kollicoat Protect (36.8 mg) | Binding Agent |
| | Hydroxypropyl Cellulose (34 mg) | Binding Agent |
| | Microcrystalline cellulose (21.1 mg) | Binding Agent |
| | Kollidon 90F (5.3 mg) | Binding Agent |
| | Cephalexin (250 mg) | Active Ingredient |
| | Watkins Mint (8 mg) | Flavoring agent (optional) |
| | Virginia Dare Cream (3 mg) | Flavoring agent (optional) |
| | Virginia Spearmint (6 mg) | Flavoring agent (optional) |
| | Menthol (2 mg) | Flavoring agent (optional) |

| Layer of dissolvable film | Ingredient (amount) | Function |
|---|---|---|
| | Creamer (4 mg) | Sweetener (optional) |
| | Honey (8 mg) | Sweetener (optional) |
| | Sucralose (6 mg) | Sweetener (optional) |
| | Acesulfame potassium (4 mg) | Sweetener (optional) |
| | Mag Sweet 100 F (1.8 mg) | Sweetener (optional) |
| Bottom Layer: | Kollicoat Protect (24 mg) | Binding Agent |
| | Kollidon 90F (10 mg) | Binding Agent |

Example 8: Multi-Layered Dissolvable Film with High Drug Load, PEA 200 mg

| Layer of dissolvable film | Ingredient (amount) | Function |
|---|---|---|
| Top Layer: | Glycerin (29.40 mg) | Lipid/Emulsifier/Plasticizer |
| | Carboxymethylcellulose (19.79 mg) | Binding Agent |
| | Kollidon 90F (44.52 mg) | Binding Agent |
| | VD Spearmint (21.59 mg) | Flavoring agent (optional) |
| | Stevia (4.95 mg) | Sweetener/excipient (optional) |
| | Menthol (0.49 mg) | Excipient (optional) |
| | Magna sweet 100 mm (0.72 mg) | Sweetener (optional) |
| Matrix (Active) Layer: | Glycerin (18 mg) | Lipid/Emulsifier/Plasticizer |
| | Carboxymethylcellulose (44.44 mg) | Binding Agent |
| | Kollidon 90F (22.22 mg) | Binding Agent |
| | PEA (200 mg) | Active Ingredient |
| | VD Spearmint (8.89 mg) | Flavoring agent (optional) |
| | Stevia (2.22 mg) | Sweetener (optional) |
| | Menthol (2.22 mg) | Excipient (optional) |

The invention claimed is:

1. A dissolvable film suitable for oral administration, consisting of:
   (a) a top layer consisting of lipid and binding agent, optional one or more structural polymers,
   (b) a matrix layer consisting of lipid, emulsifier, plasticizer, binding agent, and at least one active ingredient present in a total amount of at least about 30 wt. %, and
   (c) a bottom layer consisting of binding agent, optional one or more structural polymers, wherein,
   the top layer and the bottom layer contain between them the matrix layer,
   each of the top layer, the matrix layer, and the bottom layer is dissolvable, and
   one or more structural polymers is present at least one of top layer and the bottom layer, such that the dissolvable film is mucoadhesive.

2. The dissolvable film of claim 1, configured to disintegrate, within about 45 seconds, when placed in the mouth.

3. The dissolvable film of claim 1, configured to disintegrate within the mouth of a patient in less than about one minute.

4. The dissolvable film of claim 1, having a dissolution rate, such that when placed in the oral cavity, the dissolvable oral film will completely dissolve within about 30-300 seconds.

5. The dissolvable film of claim 1, wherein the at least one active ingredient present in a total amount of at least about 300 mg.

\* \* \* \* \*